United States Patent [19]

Baker et al.

[11] Patent Number: 4,940,703

[45] Date of Patent: Jul. 10, 1990

[54] SPIROCYCLIC COMPOUNDS INCORPORATING FIVE-MEMBERED RINGS WITH TWO HETEROATOMS FOR TREATING PSYCHOTIC DISORDERS, ETC.

[75] Inventors: Raymond Baker, Much Hadham; Clare O. Kneen, Little Walden; John Saunders, Bishops Stortford; Christopher Swain, Duxford, all of England

[73] Assignee: Merck Sharp & Dohme Limited, Hoddesdon, England

[21] Appl. No.: 333,076

[22] Filed: Apr. 4, 1989

[30] Foreign Application Priority Data

Apr. 11, 1988 [GB] United Kingdom ............... 8808433

[51] Int. Cl.$^5$ ............... A61K 31/55; C07D 451/00; C07D 453/00
[52] U.S. Cl. ............... 514/210; 514/212; 514/214; 514/278; 514/365; 514/374; 514/378; 514/409; 540/543; 546/18; 546/19; 548/147; 548/216; 548/240; 548/409; 548/410; 548/411; 548/950; 548/952; 548/953
[58] Field of Search ............... 546/18, 19; 540/543; 548/147, 216, 240, 409, 410, 411, 950, 952, 953; 514/278, 214, 212, 365, 374, 378, 409, 210

[56] References Cited

U.S. PATENT DOCUMENTS

| | | |
|---|---|---|
| 3,646,053 | 2/1972 | Poletto et al. |
| 4,104,391 | 8/1978 | Cohen et al. ............ 546/18 X |
| 4,203,990 | 5/1980 | Yen ............ 546/133 X |
| 4,342,769 | 8/1982 | Steinman et al. ............ 548/181 X |

FOREIGN PATENT DOCUMENTS

| | | |
|---|---|---|
| 2193633 | 2/1988 | United Kingdom . |
| 0083566 | 7/1983 | European Pat. Off. . |
| 0239309 | 9/1987 | European Pat. Off. . |
| 0261763 | 3/1988 | European Pat. Off. . |

*Primary Examiner*—Richard A. Schwartz
*Attorney, Agent, or Firm*—William H. Nicholson; Joseph F. DiPrima

[57] ABSTRACT

The present invention provides a compound of formula I or a salt or prodrug thereof:

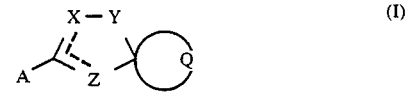

wherein the dotted line represents an optional chemical bond in one of the two possible positions;

A represents a group of formula II:

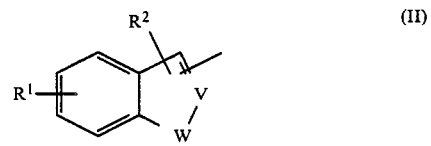

in which $R^1$ represents hydrogen, hydroxy, $C_{1-6}$ alkyl, $C_{2-6}$ alkenyl, $C_{2-6}$ alkynyl, $C_{1-6}$ alkoxy, benzyloxy, hydroxy($C_{1-6}$)alkyl, halogen, amino, cyano, nitro, —$CONR^6R^7$ or —$SO_2NR^6R^7$, in which $R^6$ and $R^7$ independently represent hydrogen, halogen, $C_{1-6}$ alkyl, $C_{2-6}$ alkenyl or $C_{2-6}$ alkynyl;

$R^2$ represents hydrogen, halogen, $C_{1-6}$ alkyl, $C_{1-6}$ alkoxy or $C_{1-6}$ alkylcarbonyl;

V represents nitrogen, —CH or —C—; and

W represents oxygen, sulphur or —$NR^8$, in which $R^8$ represents hydrogen, $C_{1-6}$ alkyl, $C_{2-6}$ alkenyl or $C_{2-6}$ alkynyl;

two of X, Y and Z are the same or different and each represents oxygen, sulphur or nitrogen; and the remaining group X, Y or Z is carbon, or Y is carbonyl (C=O); and Q is the residue of an azacyclic or azabicyclic ring system; which compounds are useful in the treatment of psychotic disorders (e.g. schizophrenia and mania); anxiety; alcohol or drug withdrawal or dependence; pain; gastric stasis; gastric dysfunction (such as occurs with dyspepsia, peptic ulcer, reflux oesophagitis and flatulence); migraine, nausea and vomiting; movement disorders; and presenile and senile dementia.

8 Claims, No Drawings

SPIROCYCLIC COMPOUNDS INCORPORATING FIVE-MEMBERED RINGS WITH TWO HETEROATOMS FOR TREATING PSYCHOTIC DISORDERS, ETC.

This invention relates to a class of spirocyclic compounds which are useful in the treatment of psychotic disorders (e.g. schizophrenia and mania); anxiety; alcohol or drug withdrawal or dependence; pain; gastric stasis; gastric dysfunction (such as occurs with dyspepsia, peptic ulcer, reflux oesophagitis and flatulence); migraine, nausea and vomiting; movement disorders; and presenile and senile dementia (also known as Alzheimer's disease and sensile dementia of the Alzheimer type respectively).

The present invention provides a compound of formula I or a salt or prodrug thereof:

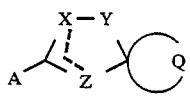
(I)

wherein the dotted line represents an optional chemical bond in one of the two possible positions;

A represents a group of formula II:

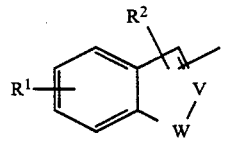
(II)

in which
R$^1$ represents hydrogen, hydroxy, C$_{1-6}$ alkyl, C$_{2-6}$ alkenyl, C$_{2-6}$ alkynyl, C$_{1-6}$ alkoxy, benzyloxy, hydroxy(C$_{1-6}$)alkyl, halogen, amino, cyano, nitro, —CONR$^6$R$^7$ or —SO$_2$NR$^6$R$^7$, in which R$^6$ and R$^7$ independently represent hydrogen, C$_{1-6}$ alkyl, C$_{2-6}$ alkenyl or C$_{2-6}$ alkynyl;

R$^2$ represents hydrogen, halogen, C$_{1-6}$ alkyl, C$_{1-6}$ alkoxy or C$_{1-6}$ alkylcarbonyl;

V represents nitrogen,

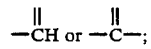

and
W represents oxygen, sulphur or

in which R$^8$ represents hydrogen, C$_{1-6}$ alkyl, C$_{2-6}$ alkenyl or C$_{2-6}$ alkynyl;

two of X, Y and Z are the same or different and each represents oxygen, sulphur or nitrogen; and the remaining group X, Y or Z is carbon, or Y is carbonyl (C=O); and Q is the residue of an azacyclic or azabicyclic ring system.

The 5-membered ring containing X, Y and Z shown in formula I may, for example, be an oxazoline, isoxazoline, thiazoline, dioxolane, oxathiolane or dithiolane ring. Preferably the ring is an oxazoline or dioxolane ring.

The group A is suitably an indole, benzofuran or benzthiophene, of formula IIA:

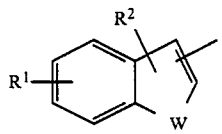
(IIA)

wherein R$^1$, R$^2$ and W are as defined above.

Preferably the group A represents an indole of structure IIB:

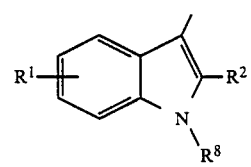
(IIB)

wherein R$^1$, R$^2$ and R$^8$ are as defined above. Preferably R$^1$ and R$^8$ independently represent hydrogen or methyl, and R$^2$ is hydrogen.

The azacyclic or azabicyclic ring system of which Q is the residue is a non-aromatic ring system containing one nitrogen atom as the sole heteroatom. Suitably the ring system contains from 4 to 10 ring atoms, preferably from 5 to 9 ring atoms. The bicyclic systems may be fused, spiro or bridged. Examples of suitable ring systems which Q completes include the following:

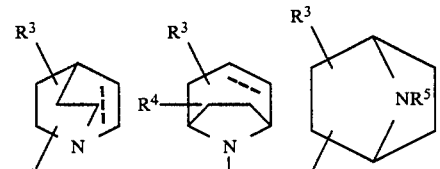

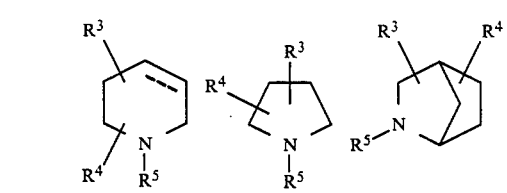

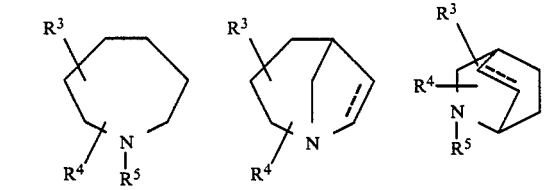

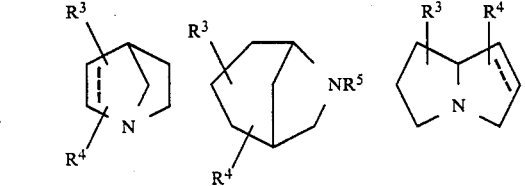

-continued

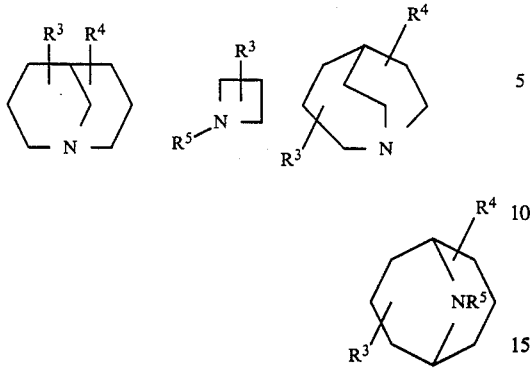

wherein the broken line represents an optional chemical bond;

$R^3$ and $R^4$ independently represent hydrogen, $C_{1-4}$ alkyl, $C_{2-4}$ alkenyl, $C_{2-4}$ alkynyl, halogen, $C_{1-4}$ alkoxy, hydroxy, carboxy or $C_{2-4}$ alkoxycarbonyl; or $R^3$ and $R^4$ together represent carbonyl; and $R^5$ represents hydrogen, benzyl, $C_{1-4}$ alkyl, $C_{2-4}$ alkenyl or $C_{2-4}$ alkynyl.

It will be appreciated that the nitrogen atom in the azacyclic or azabicyclic ring will carry a lone pair of electrons.

It will also be appreciated that the $R^3$ and $R^4$ substituents may be present at any position in the azacyclic or azabicyclic ring system; and it will further be appreciated that the point of attachment of the azacyclic or azabicyclic ring system to the five-membered ring in formula I may be at any position of the ring system.

Suitably the group $R^3$ is hydrogen or methyl; and $R^4$ is hydrogen, $C_{1-4}$ alkoxy, $C_{1-4}$ alkyl or hydroxy, preferably methoxy, methyl or hydroxy. Preferably one or both of $R^3$ and $R^4$ is hydrogen.

Suitably the azacyclic or azabicyclic ring system is pyrrolidine, piperidine, tetrahydropyridine, azanorbornane, quinuclidine, isoquinuclidine, azabicyclo[3.2.1]octane or azabicyclo[3.3.1]nonane, any of which may be optionally substituted with methyl or hydroxy.

The alkyl, alkenyl and alkynyl groups referred to with respect to any of the above formulae may represent straight, branched or cyclic groups. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkylalkyl groups such as cyclopropylmethyl; suitable alkenyl groups include vinyl and allyl; and suitable alkynyl groups include propargyl.

One sub-class of compounds within the scope of the present invention is represented by formula III:

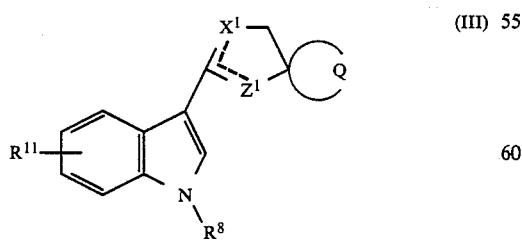

wherein $R^8$, Q and the dotted line are as defined above; $X^1$ and $Z^1$ independently represent oxygen, sulphur or nitrogen; and $R^{11}$ represents hydrogen, hydroxy, $C_{1-6}$ alkyl, $C_{1-6}$ alkoxy, halogen, amino or nitro. In particular, Q may represent the residue of an optionally substituted piperidine, azanorbornane, quinuclidine, 8-azabicyclo[3.2.1]octane or 1-azabicyclo[3.3.1]nonane ring system, wherein the $R^5$ substituent as defined above, where present, suitably represents methyl or benzyl.

Most of the compounds of this invention have at least one asymmetric centre and often more than one; and can therefore exist both as enantiomers and as diastereoisomers. In particular, those compounds possessing an unsymmetrical azabicyclic ring system may exist as exo and endo diastereoisomers. It is to be understood that the invention covers all such isomers and mixtures thereof.

Also included within the scope of the present invention are salts of the novel compounds. It will be appreciated that salts of the compounds for use in medicine will be non-toxic pharmaceutically acceptable salts. Other salts may, however, be useful for the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid or phosphoric acid. Salts of amine groups may also comprise the quaternary ammonium salts in which the amino nitrogen atom carries an alkyl, alkenyl, alkynyl or aralkyl group. Where the novel compound carries a carboxylic acid group the invention also contemplates salts thereof, preferably non-toxic pharmaceutically acceptable salts thereof, such as the sodium, potassium and calcium salts thereof.

Specific compounds of this invention include:

[2'-(methyl-1H-indol-3-yl)]spiro(1-azabicyclo[2.2.2]octane-3,5'(4'H)-oxazole);

[8-methyl-2'-(1-methyl-1H-indol-3-yl)]spiro(8-azabicyclo[3.2.1]octane-3,5'(4'H)-oxazole);

[8-benzyl-2'-(1-methyl-1H-indol-3-yl)]spiro(8-azabicyclo[3.2.1]octane-3,5'(4'H)-oxazole);

[2'-(5-fluoro-1-methyl-1H-indol-3-yl)]spiro(1-azabicyclo[2.2.2]octane-3,5'(4'H)-oxazole);

[8-methyl-2'-(5-fluoro-1-methyl-1H-indol-3-yl)]spiro(8-azabicyclo[3.2.1]octane-3,5'(4'H)-oxazole);

[2'-(1H-indol-3-yl)]spiro(1-azabicyclo[2.2.2]octane-3,5'(4'H)-oxazole);

[2'-(1-methyl-1H-indol-3-yl)]spiro(1-azabicyclo[3.3.1]nonane-4,5'(4'H)-oxazole);

[2'-(1-cyclopropylmethyl-1H-indol-3-yl)]spiro(1-azabicyclo[2.2.2]octane-3,5'(4'H)-oxazole);

[2'-(1-ethyl-1H-indol-3-yl)]spiro(1-azabicyclo[2.2.2]octane-3,5'(4'H)-oxazole);

[2'-(5-nitro-1H-indol-3-yl)]spiro(1-azabicyclo[2.2.2]octane-3,5'(4'H)-oxazole;

[2'-(1-methyl-1H-indol-3-yl)]spiro(1-methylpiperidine-4,5'(4'H)-oxazole);

[2'-(1-methyl-1H-indol-3-yl)]spiro(1-azabicyclo[2.2.1]heptane-3,5'(4'H)-oxazole);

[2'-(1-methyl-1H-indol-3-yl)]spiro(1-methyl-1-azoniabicyclo[2.2.2]octane-3,5'(4'H)-oxazole) iodide;

[2'-(benzo(b)thiophen-3-yl)]spiro(1-azabicyclo[2.2.2]octane-3,5'(4'H)-oxazole);

[2'-(1-propyn-2-yl-1H-indol-3-yl)]spiro(1-azabicyclo[2.2.2]octane-3,5'(4'H)-oxazole);

[2'-(1-propen-2-yl-1H-indol-3-yl)]spiro(1-azabicyclo[2.2.2]octane-3,5'(4'H)-oxazole);

[2'-(5-amino-1-methyl-1H-indol-3-yl)]spiro(1-azabicyclo[2.2.2]octane-3,5'(4'H)-oxazole);
2'-(2-iodo-1-methyl-1H-indol-3-yl)]spiro(1-azabicyclo[2.2.2]octane-3,5'(4'H)-oxazole);
[2'-(1H-indazol-3-yl)]spiro(1-azabicyclo[2.2.2]octane-3,5'(4'H)-oxazole);
[2'-(5-nitro-1-methyl-1H-indol-3-yl)]spiro(1-azabicyclo[2.2.2]octane-3,5'(4'H)-oxazole);
2'-(5-methoxy-1-methyl-1H-indol-3-yl)]spiro(1-azabicyclo[2.2.2]octane-3,5'(4'H)-oxazole);
[2'-(5-hydroxy-1-methyl-1H-indol-3-yl)]spiro(1-azabicyclo[2.2.2]octane-3,5'(4'H)-oxazole);
[2'-(1,5-dimethyl-1H-indol-3-yl)]spiro(1-azabicyclo[2.2.2]octane-3,5'(4'H)-oxazole);
[2'-(1,7-dimethyl-1H-indol-3-yl)]spiro(1-azabicyclo[2.2.2]octane-3,5'(4'H)-oxazole);
[2'-(1-methyl-1H-indol-3-yl)]spiro(8-azabicyclo[3.2.1]octane-3,5'(4'H)-oxazole);
[2'-(1-methyl-1H-indol-3-yl)]spiro(1-azabicyclo[2.2.2]octane-3,4'(5'H)-oxazole);
and salts and prodrugs thereof.

This invention also provides a pharmaceutical composition comprising a compound of the invention and a pharmaceutically acceptable carrier.

The compounds of the invention can be administered orally, parenterally or rectally at a daily dose of about 0.01 to 10 mg/kg of body weight, preferably about 0.1 to 1 mg/kg, and may be administered on a regimen of 1 to 4 times a day.

The pharmaceutical formulations of this invention preferably are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone and gelatin.

The oxazoline and thiazoline compounds of this invention may be prepared by a process which comprises reacting a reactive derivative of a carboxylic acid of formula A—$CO_2H$ with a compound either of formula IV or of formula V or a salt thereof:

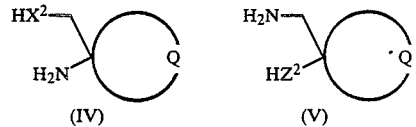

wherein $X^2$ and $Z^2$ are oxygen or sulphur; and A and Q are as defined above.

Suitable reactive derivatives of the acid A—$CO_2H$ include esters, for example $C_{1-4}$ alkyl esters; thioesters, for example pyridylthioesters; acid anhydrides, for example $(ACO)_2O$; acid halides, for example acid chlorides; orthoesters; and primary, secondary and tertiary amides.

A preferred reactive derivative of the acid A—$CO_2H$ is the iminoether derivative of formula VI:

where R is $C_{1-4}$ alkyl.

The process is conveniently effected by condensation of the starting materials in the presence of thionyl chloride, phosphorus oxychloride or triphenylphosphine/diethyl azodicarboxylate.

The intermediate of formula V may be prepared by conventional methods, for example:

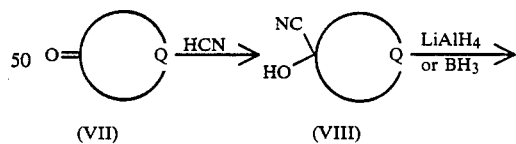

The oxazoline compounds according to the invention may alternatively be prepared by the silicon tetrafluoride-promoted reaction of a suitable oxirane with a nitrile A—CN, as described in Heterocycles, 1988, 27, 2527.

The isoxazolines according to the present invention may be prepared by reaction of a nitrile oxide of formula A—C≡N+-O− with an alkene of formula IX:

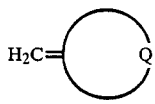

wherein A and Q are as defined above. The nitrile oxide may itself be prepared by reacting the oxime of formula A—CH(=NOH) with N-chlorosuccinimide, followed by treatment with triethylamine.

The dioxolanes, oxathiolanes and dithiolanes of this invention may be prepared by either of two alternative methods, depending on the orientation of the heteroatoms relative to the groups A and Q. One method is to react an aldehyde of formula A—CHO with a compound of formula X:

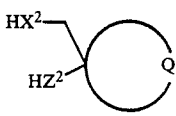

wherein $X^2$ and $Z^2$ independently represent oxygen or sulphur; and A and Q are as defined above. An alternative method is to react an azacyclic or azabicyclic ketone of formula VII with a compound of formula XI:

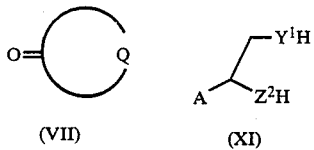

wherein $Y^1$ and $Z^2$ independently represent oxygen or sulphur; and A and Q are as defined above. Either reaction is suitably carried out in the presence of acid in an inert solvent such as benzene, toluene or dioxan.

The preparation of the intermediate of formula X from compound VIII is illustrated by the following sequence:

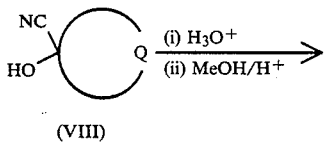

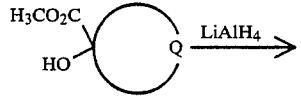

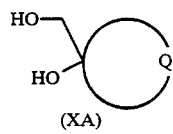

The azacyclic or azabicyclic derivatives VII and IX may be obtained by methods known from the art, in particular by methods analogous to those described in EP-A-0239309.

After any of the above described processes is complete, one substituent can be converted to another. For example an amino group may be converted to chloro, or hydrazo, —NHNH₂, via the intermediacy of diazonium, —N₂. Similarly, a chloro substituent may be converted to methoxy by reaction with a nucleophile such as methoxide; alkoxycarbonyl groups may be converted, via carboxy, to an amino substituent, —NH₂; and methoxy may be converted to hydroxy by treatment with concentrated hydrobromic acid.

In any of the above reactions it may be necessary and/or desirable to protect any sensitive groups in the compounds. For example, if the substituents include amino, carboxy, keto, hydroxy or thiol groups, these may be protected in conventional manner. Thus, suitable protecting groups for hydroxy groups include silyl groups such as trimethylsilyl or t-butyldimethylsilyl, and etherifying groups such as tetrahydropyranyl; and for amino groups include benzyloxycarbonyl and t-butoxycarbonyl. Keto groups may be protected in the form of a ketal. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be removed at any convenient stage in the synthesis of the desired compound according to conventional techniques.

The following Examples illustrate the preparation of compounds according to the invention.

The compounds according to the present invention may be evaluated for their anti-emetic activity in the von Bezold-Jarisch test (*Nature*, 1985, 316, 126), or in animal models of anxiety (see, for example, *Br. J. Pharmac.*, 1988, 93, 985), schizophrenia (see, for example, *Eur. J. Pharmac.*, 1987, 138, 303) or cognition (passive avoidance assay).

Certain of the compounds of the present invention act on 5-HT₃ receptors and this may account, in whole or in part, for the pharmacological activity of these compounds. The 5-HT₃ binding of the compounds of the invention was assayed using the protocol described in the literature (*Nature*, 1987, 330, 716) but instead of using the compound GR-65630 described therein, the ³H methylated quaternary derivative of formula XII was employed as a radioligand:

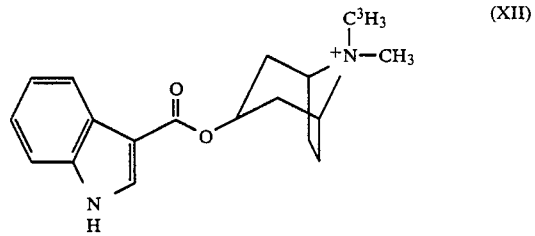

The compounds of each of the Examples demonstrate an affinity for the 5-HT₃ receptor with a $K_i$ (dissociation constant for the displacement of radioligand) better than 100 nM.

EXAMPLE 1

[2'-(1-Methyl-1H-indol-3-yl)-]spiro(1-azabicyclo[2.2.2]octane-3,5'(4'H)-oxazole) dihydrochloride hydrate

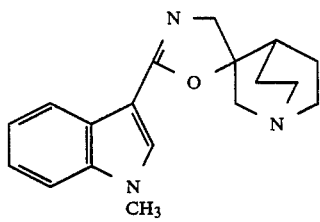

(a) Methyl (1-methyl-1H-indol-3-yl)imidate hydrochloride

Dry hydrogen chloride gas was bubbled through a solution of 1-methyl-1H-indole-3-nitrile (1.7 g) in dry methanol (30 mls). After standing at room temperature for 24 h addition of dry ether gave the title compound as colourless needles (1.8 g), m.p. 156°–8° C. (dec); $\delta_H$ (360 MHz, DMSO-d$_6$), 3.9 (3H, s, NCH$_3$), 4.3 (3H, s, OCH$_3$), 7.3 (1H, dt, J=7.4 and 1.2 Hz, CH), 7.4 (1H, dt, J=8.2 and 1.6 Hz, CH), 7.7 (1H, d, J=7.8 Hz, CH), 7.9 (1H, dd, J=6.7 and 1.1 Hz, CH), 9.0 (1H, s, CH); m/z 188 (M+).

(b) 3-Aminomethyl-3-hydroxy-1-azabicyclo[2.2.2]octane dihydrochloride

A solution of lithium aluminium hydride (1.0M solution in tetrahydrofuran, 10 mls,) in tetrahydrofuran (20 mls) was heated at reflux under nitrogen and 3-cyano-3-hydroxy-1-azabicyclo[2.2.2]octane (1.2 g,) was added portionwise. After heating at reflux for 30 min. the mixture was cooled and water (0.38 mls) was added followed by 15% sodium hydroxide solution (0.38 mls) and water (1.14 mls). The precipitate was filtered and the mother liquor evaporated in vacuo. The residue was dissolved in methanolic hydrogen chloride and, on standing, gave colourless needles (0.25 g), m.p. 318°–320° C.; $\delta_H$ (360 MHz, D$_2$O), 1.9–2.0 (2H, m, CH$_2$), 2.0–2.1 (1H, m, C$\underline{H}$H), 2.2–2.4 (2H, m, 4CH and C$\underline{H}$H), 3.2–3.4 (8H, m, $\overline{4 \times}$NCH$_2$); m/z 157 (M+H)+.

(c) [2'-(1-Methyl-1H-indol-3-yl)-]spiro(azabicyclo[2.2.2]octane-3,5'(4'H)-oxazole), dihydrochloride hydrate Methyl (1-methyl-1H-indol-3-yl)imidate hydrochloride (0.47 g,) and 3-aminomethyl-3-hydroxy-1-azabicyclo[2.2.2]octane (0.33 g, 2 mmol) were heated under nitrogen in refluxing methanol (25 mls) for 2 h and allowed to cool. After evaporation in vacuo the residue was dissolved in 2N hydrochloric acid. The solution was washed with dichloromethane basified with potassium carbonate and extracted with dichloromethane. The extract was washed (water), dried (MgSO$_4$) and solvents evaporated in vacuo. The residual solid was dissolved in methanol and methanolic hydrogen chloride added giving the title compound as colourless crystals (0.14 g), m.p. 262°–3° C. Found: C, 55.94; H, 6.29; N, 10.76; Cl, 18.39; C$_{18}$H$_{21}$N$_3$O.2HCl.H$_2$O requires C, 55.96; H, 6.52; N, 10.88; Cl, 18.35%; $\delta_H$ (360 MHz, D$_2$O), 2.00–2.30 (3H, m, CH$_2$+C$\underline{H}$H) 2.46–2.56 (1H, m, C$\underline{H}$H), 2.70–2.74 (1H, m, CH), 3.42–3.48 (2H, m, CH$_2$), 3.54–3.70 (2H, m, CH$_2$), 3.84 (1H, dd, J=15.0 and 2.1 Hz, C$\underline{H}$H), 3.96 (3H, s, NCH$_3$), 4.09 (1H, d, J=14.9 Hz, C$\underline{H}$H), 4.18 (1H, d, J=12.3 Hz, C$\underline{H}$H), 4.46 (1H, d, J=12.3 Hz, C$\underline{H}$H), 7.46 (1H, dt, J=7.4 and 1.2 Hz, CH), 7.51 (1H, dt, J=7.2 and 1.3 Hz, CH), 7.67 (1H, dd, J=7.0 and 0.8 Hz, CH), 7.93 (1H, dd, J=7.2 and 1.6 Hz, CH) 8.34 (1H, s, CH); m/z 295 (M+).

EXAMPLE 2

[8-Methyl-2'-(1-methyl-1H-indol-3-yl)-]spiro(8-azabicyclo[3.2.1]octane-3,5'-(4'H)oxazole) dihydrochloride hydrate (isomer 1)

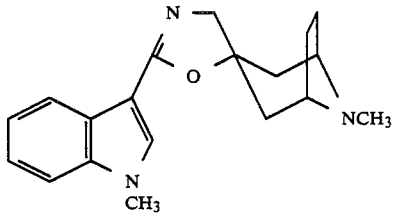

Following the method of Example 1c, methyl (1-methyl-1H-indol-3-yl)imidate hydrochloride (0.83 g, 3.7 mmol) and 3α-aminomethyl-3β-hydroxy-8-methyl-8-azabicyclo[3.2.1]octane (0.63 g, 3.7 mmol) gave the title compound, (0.25 g), m.p. 252°–3° C. Found: C, 57.21; H, 6.39; N, 10.53; Cl, 18.23; C$_{19}$H$_{23}$N$_3$O.2HCl.H$_2$O requires C, 57.00; H, 6.79; N, 10.50; Cl, 17.71%; $\delta_H$ (360 MHz, D$_2$O), 2.18–2.28 (2H, m, CH$_2$), 2.44–2.50 (2H, m, CH$_2$), 2.71 (2H, d, J=13.5 Hz, CH$_2$), 2.79 (2H, dd, J=15.3 and 3.2 Hz, CH$_2$), 2.90 and 3.18 (3H, s, NCH$_3$), 3.96 (3H, s, NCH$_3$), 4.16–4.22 (2H, m, 2×CH), 4.44 (2H, s, —NCH$_2$—), 7.46 (1H, dt, J=7.3 and 1.3 Hz, CH), 7.50 (1H, dt, J=7.7 and 1.3 Hz, CH), 7.66 (1H, d, J=7.4, CH), 7.97 (1H, dd, J=8.3 and 1.3), 8.32 (1H, s, CH); m/z 309 (M+ free base).

EXAMPLE 3

8-Methyl-[2'-(1-methyl-1H-indol-3-yl)-]spiro(8-azabicyclo[3.2.1]octane-3,5'(4'H)oxazole) dioxalate (isomer 2)

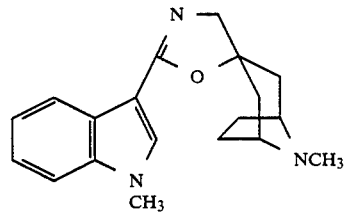

(a) 3β-Aminomethyl-3α-hydroxy-8-methyl-8-azabicyclo[3.2.1]octane dihydrochloride A mixture of 8-methyl-8-azabicyclo[3.2.1]octan-3-one (4.75 g.), trimethylsilylcyanide (5.63 mls,) and zinc iodide (0.3 g) was heated under nitrogen in dry dichloromethane (30 mls) at reflux for 24 h. After evaporation in vacuo, the residue was dissolved in dry tetrahydrofuran (20 mls) under nitrogen. To this was added a 1.0M solution of lithium aluminium hydride in tetrahydrofuran (34 mls,) and the reaction mixture was heated at reflux for 30 mins, and then chilled in ice/water. Water (1.3 mls) was added followed by 15% sodium hydroxide solution (1.3 mls) and water (3.9 mls). The precipitate was filtered and the mother liquor evaporated in vacuo. Methanolic hydrogen chloride and ether were added to give a 1:1 mixture of 3α-aminomethyl-3β-hydroxy-8-methyl-8-azabicyclo[3.2.1.]octane dihydrochloride and 3β-aminomethyl-3α-hydroxy-8-methyl-8-azabicyclo[3.2.1]octane dihydrochloride (3.7 g). Fractional crystallisation from methanol gave 3β-aminomethyl-3α-hydroxy-8-methyl-8-azabicyclo[3.2.1]octane dihydrochloride.

$\delta_H$ (360 MHz, $D_2O$), 2.13–2.24 (4H, m, 2×$CH_2$), 2.26–2.32 (2H, m, $CH_2$), 2.36–2.46 (2H, m, $CH_2$), 2.81 (3H, s, $NCH_3$), 3.00 (2H, s, $CH_2NH_2$), 3.90–4.01 (2H, m, 2×C—H).

(b)
[8-Methyl-2'-(1-methyl-1H-indol-3-yl]spiro(8-azabicyclo[3.2.1]octane-3,5'(4'H)-oxazole) dioxalate Following the method of Example 1c, 3β-aminomethyl-3α-hydroxy-8-methyl-8-azabicyclo-[3.2.1]octane (0.25 g) and methyl (1-methyl-1H-indol-3-yl) imidate hydrochloride (0.33 g) gave the title compound (0.25 g) as the free base. This was dissolved in methanol and treated with ethereal oxalic acid to give the title compound, m.p. 209°–210° C. Found: C, 56.17; H, 5.62; N, 8.54; $C_{19}H_{23}N_3O.2(CO_2H)_2$ requires C, 56.44; H, 5.56; N, 8.58%; $\delta_H$(360 MHz, $D_2O$), 2.50–2.72 (6H, m, 3×$CH_2$), 2.80 (2H, d, J=16.5 Hz, $CH_2$), 2.91 and 3.05 (3H, s, $NCH_3$), 3.97 (3H, s, $NCH_3$), 4.08 (2H, s, —$NCH_2$—), 4.10–4.18 (2H, m, 2×CH), 7.48 (1H, t, J=6.0 Hz, CH), 7.52 (1H, t, J=7.2, CH), 7.69 (1H, d, J=7.4 Hz, CH), 7.92 (1H, dd, J=6.7 and 1.6 Hz, CH), 8.37 (1H, s, CH); m/z 309 (M+, free base).

EXAMPLE 4

[8-Benzyl-2'-(1-methyl-1H-indol-3-yl)-]spiro(8-azabicyclo[3.2.1]octane-3,5'(4'H)-oxazole) dihydrochloride

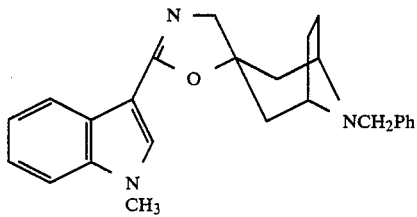

(a)
3α-Aminomethyl-3β-hydroxy-8-benzyl-8-azabicyclo[3.2.1]octane dihydrochloride Following the method of Example 1b reduction of a 1:1 mixture of 3α-cyano-3β-hydroxy-8-benzyl-8-azabicyclo-[3.2.1.]-octane and 3β-cyano-3α-hydroxy-8-benzyl-8-azabicyclo[3.2.1]octane (1.5 g) gave a mixture of products. Purification by chromatography on silica eluting with dichloromethane/MeOH/$NH_4OH$ mixtures gave the required product (0.4 g). Treatment of a methanolic solution of the amino alcohol with methanolic hydrogen chloride gave the title compound, m.p. 276°–278° C. Found: C, 56.20; H, 7.44; N, 8.67; Cl, 22.10; $C_{15}H_{22}N_2O.2HCl$ requires C, 56.43; H, 7.58; N, 8.77; Cl, 22.21%; $\delta_H$(360 MHz, $D_2O$), 2.04–2.12 (2H, m, $CH_2$), 2.17–2.34 (4H, m, 2×$CH_2$), 2.42–2.56 (2H, m, $CH_2$) 3.29 (2H, s, $CH_2NH_2$), 4.00–4.08 (2H, m, 2×CH), 4.28 (2H, bs, $CH_2Ph$), 7.55 (5H, s, 5×CH); m/z 247 (M+H)+.

(b)
[8-Benzyl-2'-(1-methyl-1H-indol-3-yl)-]spiro(8-azabicyclo[3.2.1]octan-3,5'(4'H)-oxazole)dihydrochloride hydrate Following the method of Example 1c, methyl (1-methyl-1H-indol-3-yl)imidate hydrochloride (0.37 g, 1.65 mmol) and 3α-aminomethyl-3β-hydroxy-8-benzyl-8-azabicyclo[3.2.1]octane (0.40 g,) gave the title compound (0.15 g), m.p. 179°–180° C. (dec). Found: C, 61.11; H, 6.66; N, 8.45; Cl, 14.14; $C_{25}H_{27}N_3O.2HCl.H_2O$ requires C, 60.73; H, 6.73; N, 8.50; Cl. 14.34%; $\delta_H$(360 MHz, $D_2O$) 2.22–2.34 (2H, m, $CH_2$), 2.50–2.80 (6H, m, 3×$CH_2$), 3.94 (3H, s, $NCH_3$), 4.18–4.25 (2H, m, 2×CH), 4.30–4.37 (1.5H, bs, $CH_2Ph$), 4.43 (2H, s, —$NCH_2$—), 7.42–7.52 (2H, m, 2×CH), 7.52–7.62 (5H, m, 5×CH), 7.65 (1H, d, J=7.6 Hz, CH), 7.94 (1H, d, J=7.6 Hz, CH), 8.30 (1H, s, CH); m/z 386 (M+H)+.

EXAMPLE 5

[2'-(5-Fluoro-1-methyl-1H-indol-3-yl)-]spiro(1-azabicyclo[2.2.2]octane-3,5'(4'H)oxazole) di-oxalate dihydrate (a) Methyl (5-fluoro-1-methyl-1H-indol-3-yl) imidate hydrochloride Following the method described in Example 1a 5-fluoro-1-methyl-1H-indole-3-nitrile (0.9 g) afforded the title compound (0.9 g), m.p. 159°–160° C. Found: C, 54.23; H, 5.04; N, 11.53. $C_{11}H_{11}FN_2O$ requires C, 54.44; H, 4.91; N, 11.54%; $\delta_H$ (360 MHz, $D_2O$) 3.95 (3H, s, NMe), 4.3 (3H, s, OMe), 7.26 (1H, dt, J=9.2 Hz, 2.6 Hz, CH), 7.69–7.75 (2H, m, 2×CH), 8.93 (1H, s, CH); m/z 206 (M+).

(b)
[2'-(5-Fluoro-1-methyl-1H-indol-3-yl)-]spiro(1-azabicyclo[2.2.2]octane-3,5'(4'H)oxazole) di-oxalate dihydrate Following the method described in Example 1c methyl (5-fluoro-1-methyl-1H-indol-3-yl]imidate hydrochloride (0.24 g) and 3-aminomethyl-3-hydroxy-1-azabicyclo[2.2.2]octane (0.16 g) in methanol (20 ml) afforded the title compound (100 mg); m.p. 175°–178° C.; Found: C, 50.18; H, 5.02; N, 7.81 $C_{18}H_{20}FN_3O.2(CO_2H)_2.2H_2O$ requires C, 49.91; H, 5.33; N, 7.94%; $\delta_H$ (360 MHz, $D_2O$) 2.0–2.6 (4H, m, 2×$CH_2$), 2.76 (1H, m, CH), 3.4–3.68 (4H, m, 2×$CH_2N$), 3.85 (1H, dd, J=16.8 Hz, 1.8 Hz, $CHH$N), 3.96 (3H, s, NMe), 4.12 (1H, d, J=16.8 Hz, $CH\overline{H}$N), 4.20 (1H, d, J=12 Hz, $CHH$N), 4.49 (1H, d, J=12 Hz, $CH\overline{H}$N), 7.27 (1H, dt, J=9.3 Hz, 2.5 Hz, CH), 7.59 (1H, dd, J=9.3 Hz, 2.5 Hz, CH), 7.64 (1H, dd, J=9.4 Hz, 2.4 Hz, CH), 8.41 (1H, s, CH); m/z 313 (M+, free base).

EXAMPLE 6

[8-Methyl-2'-(5-fluoro-1-methyl-1H-indol-3-yl)-]spiro(8-azabicyclo[3.2.1]octane-3,5'(4'H)oxazole) dioxalate hemihydrate (isomer 1) and [8-methyl-2'-(5'-fluoro-1-methyl-1H-indol-3-yl)-]spiro(8-azabicyclo[3.2.1]octane-3,5'(4'H)-oxazole) di-oxalate hemihydrate (isomer 2)

Following the method described in Example 1c methyl (5-fluoro-1-methyl-1H-indol-3-yl)imidate hydrochloride (0.48 g) and 3-aminomethyl-3-hydroxy-8-methyl-8-azabicyclo[3.2.1]octane (0.34 g) in methanol (20 ml) afforded the title compounds (isomer 1) (40 mg), m.p. 125°–128° C. Found: C, 53.09; H, 4.96; N, 8.04. $C_{21}H_{24}FN_3O_9.0.5H_2O$ requires C, 53.49; H, 5.27; N, 8.14%; $\delta_H$ (360 MHz, D$_2$O) 2.17–2.50 (4H, m, 2×CH$_2$), 2.71 (2H, d, J=15 Hz, CH$_2$), 2.79 (2H, dd, J=18 Hz, 3.5 Hz, CH$_2$), 2.89 (3H, s, NMe), 3.95 (3H, s, NMe), 4.14–4.22 (2H, m, 2×CHN), 4.44 (2H, s, CH$_2$), 7.25 (1H, dt, J=10 Hz, 3 Hz, CH), 7.6–7.65 (2H, m, 2×CH), 8.36 (1H, s, CH); m/z 327 (M+, free base); and (isomer 2) (0.26 g), m.p. 185°–186° C. Found C, 53.18; H, 5.52; N, 7.83 C$_{21}$H$_{21}$FN$_3$O$_9$.0.5H$_2$O requires C, 53.48; H, 5.27; N, 8.14%; $\delta_H$ (360 MHz, D$_2$O) 2.5–2.8 (8H, m, 4×CH$_2$), 2.91 (3H, s, NCH$_3$), 3.96 (3H, s, NMe), 4.08 (2H, s, CH$_2$), 4.10–4.18 (2H m, 2×CHN), 7.27 (1H, dt, J=9.3 Hz, 2.4, CH), 7.5–7.65 (2H, m, 2×CH), 8.38 (1H, s, CH); m/z 327 (M+, free base).

EXAMPLE 7

[2'-(1H-Indol-3-yl)-]spiro(1-azabicyclo[2.2.2]octane-3,5'(4'H)-oxazole) dihydrochloride sesquihydrate (a) Methyl (1H-indol-3-yl)imidate hydrochloride Following the procedure described in Example 1a 1H-indole-3-nitrile (2.0 g) afforded the title compound (1.8 g), m.p. 165–167° C. (dec), $\delta_H$ (360 MHz, DMSO-d$_6$), 4.30 (3H, s, OMe), 7.26–7.33 (2H, m, 2×CH), 7.6 (1H, dd, J=6.0 Hz, 1.6 Hz, CH), 7.93 (1H, dd, J=8.4 Hz, 2.0Hz, CH), 8.9 (1H, d, J=2 Hz, CH), 10.4, 11.4 (2H, 2×bs, 2×NH); m/z 174 (+, free base), 143 (100, M+-OMe).

(b) [2'-(1H-Indol-3-yl)-]spiro(1-azabicyclo[2.2.2]octane-3,5'(4'H)-oxazole) dihydrochloride sesquihydrate Following the procedure described in Example 1c methyl (1H-indol-3-yl)imidate (0.67 g) and 3-aminomethyl-3-hydroxy-1-azabicyclo[2.2.2]octane (0.5 g) in methanol (70 ml) gave the title compound (1.0 g); m.p. 220–222° C. Found: C, 52.72; H, 6.34; N, 10.91 C$_{17}$H$_{19}$N$_3$O.2HCl.1.5H$_2$O requires C, 53.04; H, 6.31; N, 10.92%; $\delta_H$ (360 MHz, D$_2$O) 2.0 – 2.58 (4H, m, 2×CH$_2$), 2.78 (1H, m, CH), 3.4–3.5 (2H, m, CH$_2$N), 3.56–3.72 (2H, m, CH$_2$N), 3.86 (1H, dd, J=15 Hz, 2 Hz, CHHN), 4.13 (1H, d, J=15 Hz, CHHN), 4.22 (1H, d, J=12 Hz, CHHN), 4.50 (1H, d, J=12 Hz, CHHN), 7.4–7.48 (2H, m, 2×CH), 7.7 (1H, m, CH), 7.95 (1H, m, CH), 8.48 (1H, s, CH); m/z 281 (M+, free base).

EXAMPLE 8

[2'-(1-Methyl-1H-indol-3-yl)-]spiro(1-azabicyclo[3.3.1]nonane-4,5'(4'H)-oxazole) dihydrochloride (a) 1-Carbomethylethyl-3-carboethoxyethylpiperidine Ethyl ipecotate (51 g) in toluene (50 ml) was added dropwise to a slurry of anhydrous potassium carbonate (89 g) in toluene (200 ml) and stirred for 15 minutes. Ethyl-3-bromopropionate (58.6 g) in toluene (50 ml) was added dropwise and reaction mixture heated at reflux for 3 hours once addition was complete. The mixture was then cooled and toluene decanted. The residual toluene and inorganics were mixed with water (300 ml) and extracted with dichloromethane (3×200 ml). The combined organic layers were dried (MgSO$_4$), filtered and concentrated to a yellow oil (70 g). $\delta_H$(360 MHz, CDCl$_3$), 1.25 (6H, 2×t, J=7.2 Hz and J=7.2 Hz, 2×CH$_3$), 1.4–1.9 (4H, m, 2×CH$_2$), 2.0–2.1 (1H, m, CH), 2.2 (1H, m, NCHH), 2.5 (2H, t, J=7.4 Hz, CH$_2$CO), 2.55 (1H, m, NCHH), 2.70 (2H, t, J=7.3 Hz, NCH$_2$), 2.75 (1H, m, NCHH), 2.95 (1H, br d, NCHH), 4.1 (4H, 2×q, J=7.1 Hz and J= 7.1 Hz, 2×OCH$_2$); m/z 258 (M+ +H, 40%).

(b) 1-Azabicyclo[3.3.1]nonan-4-one

Anhydrous potassium t-butoxide (45.8 g) in anhydrous toluene (1.0 dm$^3$) was heated at reflux and 1-carboethoxyethyl-3-carboethoxyethylpiperidine (35.0 g) in toluene (250 ml) was added over 2 hours. Reflux was maintained for a further 4 hours before cooling to room temperature and concentrated hydrochloric acid (300 ml) was added. The mixture was stirred for 1 hour, then the organic layer was separated and extracted with concentrated hydrochloric acid (225 ml×4). The combined acid extracts were heated at reflux for 16 hours, then basified to pH 10 with potassium carbonate and extracted with chlorofeny (300 ml×6). The combined organic extracts were dried (MgSO$_4$) and concentrated in vacuo to an orange semi-solid (9.7 g). This was purified by chromatography (Alumina grade III) by gradient elution in 3–10% methanol in ethyl acetate. The title compound was isolated as light orange semi-solid (3.5 g). $\delta_H$ (360 MHz, CDCl$_3$), 1.55 (1H, m, CHH), 1.7–1.8 (1H, m, CHH), 1.95 (2H, m, CH$_2$), 2.4 (1H, s, CH), 2.55 (2H, m, CH$_2$CO), 3.1–3.4 (6H, m, 3×CH$_2$N); m/z 139 (M+) (100%).

(c) 4-Aminomethyl-4-hydroxy-1-azabicyclo[3.3.1]nonane

Trimethylsilyl cyanide (3 ml) was added dropwise to a stirred solution of 1-azabicyclo[3.3.1]nonan-4-one (2.5 g) and zinc iodide (0.15 g) in dry dichloromethane (20 ml) and the resulting mixture was heated at reflux for 4 hours. The mixture was cooled and the solvent removed at reduced pressure; the residue was dissolved in dry tetrahydrofuran (20 ml) and cooled to 0° C. A solution of lithium aluminium hydride in tetrahydrofuran (18 ml of 1.0M soln) was then added and the resulting solution stirred overnight at room temperature. Water (0.7 ml), followed by 15% sodium hydroxide (aq) (0.7 ml) and water (2.1 ml) were then added and the precipitate removed by filtration. Evaporation of the filtrate yielded the title compound (2.2 g); $\delta_H$ (360 MHz, CDCl$_3$) 1.2–1.3 (2H, m, CH$_2$), 1.34 (1H, m, CHH), 1.41 (1H, m, CHH), 1.6 (2H, m, CH$_2$), 1.7–1.74 (1H, m, CHH), 1.76–1.91 (2H, m, CH$_2$), 2.11–2.16 (1H, m, CHH), 2.67–3.18 (8H, m); m/z 170 (M+).

(d) [2'-(1-Methyl-1H-indol-3-yl)-]spiro(1-azabicyclo[3.3.1]nonane-4,5'(4'H)-oxazole dihydrochloride Following the method described in Example 1c methyl (1-methylindol-3-yl)imidate (2.65 g) and 4-aminomethyl-4-hydroxy-1-azabicyclo[3.3.1]nonane (2.0 g) in methanol (150 ml) yielded the title compound (0.7 g), m.p. 257°–259° C. Found: C, 59.17; H, 6.55; N, 10.84. C$_{19}$H$_{23}$N$_3$O.2HCl.0.25H$_2$O requires C, 58.99; H, 6.64; N, 10.86%; $\delta_H$ (360 MHz, D$_2$O) 2.02–2.16 (2H, m, CH$_2$), 2.42–2.58 (2H, m, CH$_2$), 2.72 (1H, m, CH), 3.02 (1H, dt, J=14 Hz, 7.4 Hz, CHH), 3.48 (1H, d, J=14 Hz, CHH), 3.6–3.8 (5H, m), 3.98 (3H, s, NMe), 4.19 (1H, d, J=11.3 Hz, CHH), 4.29 (1H, d, J=11.3 Hz, CHH), 7.4–7.5 (2H, m, H-5, H-6), 7.68 (1H, d, J=7 Hz, H-7), 7.99 (1H, d, J=7 Hz, H-4), 8.39 (1H, s, H-2); m/z 309 (M+, free base).

EXAMPLE 9

[2'-(1-Cyclopropylmethyl-1H-indol-3-yl]spiro(1-azabicyclo[2.2.2]octane-3,5'(4'H)-oxazole) dihydrochloride hydrate

(a) 1-Cyclopropylmethyl-1H-indole-3-carboxylic acid

Powdered sodium hydroxide (10 g) was added cautiously to a stirred solution of indole-3-carboxylic acid (5 g) and (bromomethyl)cyclopropane (10 g) in dry acetone (50 ml). The mixture was stirred for 24 hours at room temperature then diluted with water (250 ml) and washed with dichloromethane (2×100 ml). The aqueous phase acidified to pH 2 and the precipitate isolated and dried (6.3 g), m.p. 157° C.; $\delta_H$ (360 MHz, CDCl$_3$) 0.02–0.04 (2H, m, CH$_2$), 0.18–0.28 (2H, m, CH$_2$), 0.83–0.89 (1H, m, CH), 3.57 (2H, d, J=7 Hz, NCH$_2$), 6.7–6.8 (2H, m, H-5, H-6), 6.9 (1H, d, J=7 Hz, H-7), 7.55 (1H, s, H-2), 7.72 (1H, d, J=7 Hz, H-4); m/z 215 (M$^+$, 100%), 174 (60), 144 (40).

(b) 1-Cyclopropylmethyl-1H-indole-3-carboxamide

Oxalyl chloride (3.7 g) was added slowly to a stirred solution of the carboxylic acid (6.3 g) in dry tetrahydrofuran (50 ml) at 0° C. The resulting red solution was then stirred overnight at room temperature. The solvent was evaporated at reduced pressure and the residue dissolved in dry dichloroethane (50 ml); ammonia was bubbled through the solution for 1 hr and the mixture stirred at room temperature for 12 hrs. The solvent was evaporated at reduced pressure and the residue triturated with water, then ether and dried, (5.2 g), m.p. 170° C.; $\delta_H$ (60 Mz, CDCl$_3$) 0.38–0.42 (2H, m, CH$_2$), 0.53–0.58 (2H, m, CH$_2$), 0.85–0.89 (1H, m, CH), 4.05 (2H, d, J=7 Hz, NCH$_2$), 7.09–7.20 (2H, m, H-5, H-6), 7.54 (1H, d, J=7 Hz, H-7), 8.11 (1H, s, H-2), 8.14 (2H, d, J=6, H-4); m/z 214 (M$^+$, 100%), 143 (50), 161 (30).

(c) 1-Cyclopropylmethyl-1H-indole-3-nitrile

Trifluoroacetic anhydride (19.5 g) was added dropwise to a cooled (0° C.), stirred solution of 1-cyclopropylmethyl-1H-indole-3-carboxamide (5 g) in dioxane (100 ml) and triethylamine (18 g). After the addition the mixture was stirred at room temperature for two hours, the mixture was diluted with dichloromethane (200 ml) and washed with water (3×100 ml), dried (Na$_2$SO$_4$) and evaporated at reduced pressure. The residue was purified by column chromatography on silica eluting with dichloromethane to afford a colourless oil, (5 g); $\delta_H$ (CDCl$_3$, 60 MHz) 0.3–0.6 (4H, m, 2×CH$_2$), 0.9 (1H, m, CH), 4.0 (2H, d, J=7, CH$_2$), 7.0–7.7 (5H, m); $\nu_{max}$ 2210 (C≡N).

(d) Methyl (1-cyclopropylmethyl-1H-indole-3-yl) imidate

Following the procedure described in Example 1a 1-cyclopropylmethyl-1H-indole-3-nitrile (1 g) afforded the title compound (0.8 g), m.p. 131° C.; $\delta$ (360 MHz, DMSO-d$_6$) 0.4–0.6 (4H, m, 2×CH$_2$) 1.29–1.34 (1H, m, CH), 4.15 (2H, d, J=7 Hz, NCH$_2$), 4.30 (3H, s, OMe), 7.32–7.38 (2H, m, H-5, H-6), 7.74 (1H, d, J=7 Hz, H-4), 7.96 (1H, d, J=7, H-7), 9.17 (1H, s, H-2); m/z 264 (M$^+$).

(e) [2'-(1-Cyclopropylmethyl-1H-indol-3-yl)]spiro(1-azabicyclo[2.2.2]octane-3,5'(4'H)-oxazole) dihydrochloride dihydrate Following the procedure described in Example 1c methyl (1-cyclopropylmethyl-1H-indol-3-yl)imidate hydrochloride (0.5 g) and 3-aminomethyl-3-hydroxy-1-azabicyclo[2.2.2]octane (0.5 g) was reacted in methanol (20 ml) and afforded the title compound (0.5 g); m.p. 199° C.; Found C, 57.02; H, 7.01; N, 9.35.C$_{21}$H$_{31}$N$_3$O$_3$Cl$_2$ requires C, 56.76; H, 7.03; N, 9.46%; $\delta_H$ (360 MHz, CDCl$_3$) 0.44–0.48 (2H, m, CH$_2$), 0.66–0.71 (2H, m, CH$_2$), 1.39–1.43 (1H, m, CH), 2.08–2.26 (3H, m, CH$_2$CHH), 2.53 (1H, m, CHH), 2.77 (1H, bs, CH), 3.43 (2H, m, CH$_2$N), 3.63 (2H, m, CH$_2$N), 3.87 (1H, d, J=12 Hz, CHHN), 4.13 (1H, d, J=12 Hz, CHHN), 4.20–4.24 (4H, m, NCH$_2$, CHH), 4.50 (1H, d, J=10 Hz, CHH), 7.4–7.53 (2H, m, H-5, H-6), 7.75 (1H, d, J=6 Hz, H-7), 7.96 (1H, d, J=6 Hz, H-7), 8.65 (1H, s, H-2); m/z 335 (M$^+$, free base).

EXAMPLE 10

[2'-(1-Ethyl-1H-indol-3-yl)-]spiro(1-azabicyclo[2.2.2]octane-3,5'(4'H)-oxazole) dihydrochloride dihydrate

(a) Methyl (1-ethyl-1H-indol-3-yl) imidate hydrochloride

Following the procedure described in Example 1a 1-ethyl-1H-indole-3-nitrile (0.6 g) afforded the title compound (0.3 g), m.p. 144°–145° C.; $\delta_H$ (360 MHz, D$_2$O) 1.44 (3H, t, J=7 Hz, CH$_3$), 3.3 (2H, brs, NH$_2$), 4.30–4.37 (5H, m, NCH$_2$, OMe), 7.30–7.39 (2H, m, H-5, H-6), 7.72 (1H, d, J=7 Hz, H-7), 7.93 (1H, d, J=6 Hz, H-4), 9.10 (1H, s, H-2); m/z 202 (M$^+$, free base), 171 (85), 155 (100).

(b) [2'-(1-Ethyl-1H-indol-3-yl)-]spiro(1-azabicyclo[2.2.2]octane-3,5'(4'H)-oxazole hydrochloride dihydrate Following the procedure described in Example 1c methyl (1-ethyl-1H-indol-3-yl)imidate hydrochloride (0.3 g) and 3-aminomethyl-3-hydroxy-1-azabicyclo[2.2.2]octane (0.2 g), in methanol (20 ml) afforded the title compound (0.2 g); m.p. 194°–196° C.

EXAMPLE 11

[2'-(1-Methyl-1H-indol-3-yl)-spiro(1-azabicyclo[2.2.2]octane-3,5'(4'H)-oxazole) dihydrochloride

(a) 3-Cyano-3-hydroxyquinuclidine

To a cooled (ice bath), stirred solution of 3-quinuclidinone hydrochloride (300 g) in water (400 ml) was added dropwise a solution of sodium cyanide (90.97 g) in water (400 ml). After stirring at ice bath temperature for three hours the precipitate was collected by filtration, washed with water and dried under vacuum to afford the title compound (282 g); m.p. 153°–157° C. (lit m.p. 152°–155° C.; Helv. Chim. Acta., 1954, 37, 1689).

(b) 3-Aminomethyl-3-hydroxy-1-azabicyclo[2.2.2]octane borane complex

A solution of borane in tetrahydrofuran (266 ml), of a 1.0M solution, was added to a stirred solution of 3-cyano-3-hydroxyquinuclidine (40 g) in tetrahydrofuran (400 ml) under nitrogen. When the borane complex had formed (tlc monitor) two further equivalents of borane in tetrahydrofuran were added (534 ml), and the reaction heated at reflux for 12 hr. The mixture was cooled to room temperature and ethanol (500 ml) added slowly; the resulting solution was stirred at room temperature for 12 hr. The solvent was then removed at reduced pressure and the residue recrystallised from ethanol to afford the title compound as a white crystalline solid (32 g), m.p. 163° C.; $\delta_H$ (360 MHz, CDCl$_3$) 1.16-1.61 (3H, m, CH, CHH), 1.86 (1H, m, CHH), 2.05 (1H, m, CH), 2.4-2.97 (8H, m, 4×CH$_2$N); m/z 157 (M+).

(c) [2'-(1-Methyl-1H-indol-3-yl)-]spiro(1-azabicyclo[2.2.2]octane-3,5'(4'H)-oxazole) dihydrochloride A solution of methyl (1-methyl-1H-indol-3-yl) imidate hydrochloride (22.45 g) in anhydrous methanol (350 ml) was added to a stirred solution of 3-aminomethyl-3-hydroxy-1-azabicyclo[2.2.2]octane borane complex (20.4 g) in methanol (350 ml) under nitrogen over 75 mins. The resulting solution was then heated at reflux for 12 hr and allowed to cool to room temperature. Saturated methanolic hydrogen chloride was added (100 ml) and the mixture heated at reflux for 12 hr. The solvent was removed under reduced pressure and the residue dissolved in 2N hydrochloric acid (50 ml) and water (200 ml). The solution was washed with dichloromethane (250 ml), basified with ammonium hydroxide and extracted with dichloromethane (3×100 ml). The combined extracts were dried (Na$_2$SO$_4$) and the solvent removed at reduced pressure. The residue was purified on silica eluting with dichloromethane/methanol/NH$_4$OH (90:10:1) to afford the title compound as a viscous oil (19.5 g, 66%); $\delta_H$ (CDCl$_3$) 1.5-1.58 (3H, m, CH$_2$, CHH), 2.01 (1H, m, CHH), 2.17 (1H, m, CH), 2.82 (2H, m, CH$_2$N), 2.97 (1H, d, J=15, CHHN), 3.0 (2H, m, CH$_2$N), 3.31 (1H, d, J=15, CHHN), 3.76 (1H, d, J=12, CHN), 3.82 (3H, s, NMe), 4.19 (1H, d, J=12, CHHN), 7.22-7.35 (3H, m, Ar), 7.63 (1H, s, H-2), 8.16 (1H, m, Ar); m/z 295 (M+).

EXAMPLE 12

(+)[2'-(1-Methyl-1H-indol-3-yl)-]spiro(1-azabicyclo[2.2.2]octane-3,5'(4'H)-oxazole) and (−)[2'-(1-Methyl-1H-indol-3-yl)-]spiro(1-azabicyclo[2.2.2]octane-3,5'(4'H)-oxazole)

To a solution of [2'-(1-methyl-1H-indol-3-yl)-]spiro(1-azabicyclo[2.2.2]octane-3,5'(4'H)-oxazole (6.40 g, 21.7 mmol) in a minimum of ethanol was added a solution of (+)-O,O'-dibenzoyl-D-tartaric acid (1.93 g, 5.4 mmol). The salt which crystallised was filtered and recrystallised from ethanol to constant rotation $[\alpha]_D^{20}$ +11.6° (c=0.5, MeOH). The mother liquors from the original crystallisation were evaporated to dryness, taken up in dichloromethane (200 ml) and washed with aqueous sodium bicarbonate (3×100 ml). The organic phase was dried (MgSO$_4$) and evaporated. The residue was dissolved in ethanol (20 ml) and treated with a solution of (−)-O,O'-dibenzoyl-L-tartaric acid (1.93 g, 5.4 mmol) in a minimum of ethanol. The salt which crystallised was recrystallised to constant rotation (four recrystallisations from ethanol). $[\alpha]_D^{20}$ −12.4° (c=0.5, MeOH). The (+)-salt was dissolved in dichloromethane (100 ml) and washed with dilute aqueous ammonia solution (3×100 ml). The organic phase was dried (MgSO$_4$) and evaporated to dryness. The residue was dissolved in methanol and treated with ether/HCl to give the dihydrochloride salt which was crystallised from ethanol/ether to give the title compound m.p. 261°-261° C. $[\alpha]_D^{20}$ −43.3° (c=0.5 MeOH. The (−)-salt was treated similarly to give colourless crystals m.p. 261°-262° C. $[\alpha]_D^{20}$ +43.3° (c=0.5, MeOH).

EXAMPLE 13

[2'-(5-Nitro-1H-indol-3-yl)-]spiro(1-azabicyclo[2.2.2]octane-3,5'(4H)-oxazole) dihydrochloride (a) 5-Nitro-1H-indole-3-carboxylic acid Trifluoroacetic anhydride (21.37 g) was added dropwise to a chilled solution of 5-nitro-1H-indole (15.0 g) in dry dimethylformamide (150 ml) under a dry N$_2$ atmosphere. The solution was allowed to warm to room temperature, and was then heated at reflux for 24 hours. The reaction mixture was cooled and poured into water (500 ml) and the resulting dark brown precipitate was filtered, suspended in water (200 ml) containing sodium hydroxide (50.0 g), and heated at reflux for 3 hours. The dark brown solution was cooled to room temperature, extracted with ether (4×100 ml), acidified to pH2 and the title compound filtered and dried (19 g), m.p. 256°-258° C. $\delta_H$ (360 MHz, DMSO-d$_6$) 7.71 (1H, d, J=7.2 Hz, H-7), 8.9 (1H, dd, J=7.2, 1.0 Hz), 8.27 (1H, s, H-2), 8.89 (1H, d, J=1.0 Hz, H-4); m/z 206 (M+, 70), 163 (10), 138 (20), 123 (100, 106 (15), 81 (10%).

(b) 5-Nitro-1H-indole-3-carboxamide

Oxalyl chloride (1.87 g) was added to a solution of 5-nitro-1H-indole-3-carboxylic acid (3.06 g) in dry tetrahydrofuran (80 ml). The solution was stirred at room temperature for 24 hours and then evaporated to dryness. The residue was taken up in 1,2-dichloroethane (50 ml) and anhydrous NH$_3$ gas passed through the solution for one hour, to afford the title compound as a bright yellow precipitate which was filtered and dried (3.2 g), m.p. 284°-288° C. $\delta_H$(360 MHz, DMSO-d$_6$) 7.62 (1H, d, J=7.0 Hz, H-7), 8.04 (1H, dd, J=7, 1.0 Hz, H-6), 8.29 (1H, s, H-2), 9.08 (1H, d, J=1.0 Hz, H-4); m/z 205 (M+, 90), 189 (100), 159 (10), 143 (80), 142 (80), 130 (10), 114 (40), 87 (40), 76 (20).

(c) 5-Nitro-1H-indole-3-carbonitrile

5-Nitro-1H-indole-3-carboxamide (2.0 g) was suspended in dry dioxane (100 ml) containing triethylamine (7.8 g). Trifluoroacetic anhydride (8.2 g) was added dropwise with the temperature of the solution maintained at less than 5° C., the reaction was then allowed to warm to room temperature overnight. The reaction mixture was diluted with dichloromethane (200 ml), washed with water (3×100 ml), dried (MgSO$_4$) and the solvent removed. Recrystallisation of the residue from ethyl acetate/hexane afforded the title compound (840 mg), m.p. 186°-190° C. $\delta_H$(360 MHz, CDCl$_3$) 7.58 (1H, d, J=7.2 Hz, H-7), 7.94 (1H, d, J=1.0 Hz, H-4), 8.16 (1H, dd, J=7.2, 1.0 Hz, H-6), 8.63 (1H, s, H-2); m/z 187 (M+, 100), 157 (45), 141 (95), 129 (30), 114 (55), 102 (10), 87 (20 ).

(d) Methyl (5-nitro-1H-indole-3-yl)imidate hydrochloride

Dry hydrogen chloride gas was passed through a solution of 5-nitro-1H-indole-3-carbonitrile (2.6 g) in dry methanol (100 ml) for one hour. The solution was then allowed to stand at room temperature under a dry N$_2$ atmosphere for 24 hours, during which time a purple precipitate formed. The precipitate was filtered and recyrstallised from acetone to give the title compound as pink needles (2.09 g), m.p. 220° C. dec. $\delta_H$(360 MHz, DMSO) 3.07 (3H, s, —OCH$_3$), 7.63 (1H, d, J=10.0 Hz, H-7), 8.06 (1H, dd, J=10.0, 2.5 Hz, H-6), 8.29 (1H, d, J=5.0 Hz, H-2), 4.13 (1H, d, J=2.5 Hz, H-4); m/z 219

(M+, 55), 205 (10), 188 (85), 174 (20), 158 (30), 142 (100), 129 (35), 114 (60), 87 (25), 76 (15).

(e) [2'-(5-Nitro-1H-indol-3-yl)-]spiro(1-azabicyclo[2.2.2]octane-3,5'(4'H)-oxazole) borane complex Methyl (5-nitro-1H-indol-3-yl)imidate hydrochloride (930 mg) and 3-hydroxy-3-aminomethyl-1-azabicyclo[2.2.2]octane borane complex (742 mg) were dissolved in dry methanol (80 ml) and the resulting solution heated at reflux for 12 hours, cooled to room temperature and the solvent removed. The residue was chromatographed on silica gel using dichloromethane/methanol/ammonium hydroxide as eluant to afford the title compound as a yellow solid, m.p. 290° C. (dec) $\delta_H$ (360 MHz, CDCl$_3$) 1.78 (3H, bm, CH$_2$CH$_2$N), 2.08 (1H, bm, CH-CH$_2$CH$_2$N), 2.1 (1H, bm, $\overline{CH_2}$CH$_2$N), 2.91–3.2 (6H, $\overline{bm}$, CH$_2$CH$_2$N), 3.89 (1H, $\overline{d,}$ (C=N-CH$_2$), 4.11 (1H, d, J=15.0 Hz, C=N-CH$_2$), 7.65 (1H, $\overline{d,}$ J=10.0 Hz, H-7), 8.09 (1H, dd, J=10.0, 2.5 Hz, H-6), 8.18 (1H, s, H-2), 10.37 (1H, d, J=2.5 Hz, H-4); m/z (C$_{17}$H$_{21}$N$_4$O$_3$B=340) 326 (M+-14, 10%), 189 (60), 142 (60), 114 (40), 96 (100), 82 (60).

(f) [2'-(5-Nitro-1H-indol-3-yl)-]spiro(1-azabicyclo[2.2.2]octane-3,5'(4'H)-oxazole hydrochloride The aforementioned borane complex (300 mg) was dissolved in methanol (50 ml) previously saturated with hydrogen chloride gas. The solution was heated at reflux for 12 hours, then cooled and the solvent removed. The residue was dissolved in water (50 ml), washed with dichloromethane (4×50 ml), basified to pH12 with ammonium hydroxide, extracted with dichloromethane (4×50 ml), and dried (MgSO$_4$). Filtration and removal of solvent afforded a yellow solid. Purification by flash chromatography on silica gel using dichloromethane/methanol/ammonium hydroxide as eluant afforded the free base which was further purified by treatment with a solution of ethereal hydrogen chloride and crystallisation from ethanol to afford the title compound (100 mg), m.p. 260° C. (dec); Found: C, 51.43; H, 5.21; N, 13.97 C$_{17}$H$_{20}$N$_4$O$_3$Cl$_2$ requires C, 51.3; H, 5.04; N, 14.03%; $\delta_H$ (360 Mz, D$_2$O) 2.1–2.52 (4H, bm, CH$_2$CH$_2$N), 2.79 (1H, bm, CHCH$_2$CH$_2$N), 3.2–4.1 (6H, $\overline{bm}$, CH$_2$CH$_2$N), 4.27 (1H, $\overline{d,}$ J=14.4 Hz, C=N-CH$_2$), 4.55 ($\overline{1H,}$ d, J=14.4 Hz, C=N$\cdot$CH$_2$), 7.65 (1H, $\overline{d,}$ J=10.8 Hz, H-7), 7.98 (1H, dd, J=10.8, 3.6 Hz, H-6), 8.51 (1H, s, H-2), 8.8 (1H, d, J=3.6 Hz, H-4); m/z 326 (M+, 40), 250 (20), 224 (100), 183 (30), 157 (50), 139 (50), 87 (40).

EXAMPLE 14

2'-(1-Methyl-1H-indol-3-yl)spiro[1-methyl piperidine-4,5'(4'H)-oxazole] dihydrochloride 2.25 hydrate To a chilled solution of 4-cyano-4-hydroxy-1-methyl-piperidine (1.4 g.) in tetrahydrofuran (20 ml) under nitrogen was added borane-tetrahydrofuran complex (1.0M in tetrahydrofuran, 12 ml). After stirring at room temperature for 15 minutes a further 24 ml of borane-tetrahydrofuran complex was added. After heating at reflux for 1.5 hours the reaction mixture was cooled and ethanol (25 ml) added. After stirring for 30 minutes the mixture was evaporated to dryness. The residue was dissolved in methanol (20 ml) and added dropwise to a solution of methyl (1-methyl-1H-indol-3-yl)imidate (0.43 g, 1.9 mmol) in methanol (30 ml) stirred under nitrogen. After refluxing for 24 hours the reaction mixture was evaporated to dryness and the residue purified by column chromatography on silica eluting with dichloromethane/methanol/ammoniumhydroxide mixtures to give a colourless oil. This oil was dissolved in methanol and treated with ethereal hydrogen chloride to give the title compound as a colourless crystalline solid (0.26 g), m.p. 238°–240° C.; Found: C, 51.12; H, 6.96; N, 10.47; Cl, 18.09; C$_{17}$H$_{21}$N$_3$O.2HCl. 2.25H$_2$O requires C, 51.45; H, 6.99; N, 10.59; Cl, 17.97%; $\delta_H$ (360 MHz, D$_2$O) 2.28–2.44 (2H, m) and 2.44–2.58 (2H, m, two CH$_2$), 3.06 (3H, s, N—CH$_3$), 3.44–3.56 (2H, m) and 3.64–3.76 (2H, m, two N—CH$_2$), 3.96 (3H, s, N—CH$_3$), 4.03 (2H, s, CH$_2$), 7.44–7.54 (2H, m, two CH), 7.67 (1H, d, J=7.6 Hz, CH), 7.98 (1H, d, J=8.3, CH), 8.29 (1H, s, CH); m/z 283 (M+).

EXAMPLE 15

2'-(1-Methyl-1H-indol-3-yl)spiro (3(R*), 4(R*)-1-azabicyclo[2.2.1]heptane-3,5'(4'H)-oxazole) dihydrochloride hydrate (a) 3(R*), 4(R*)-3-amino methyl-3-hydroxy-1-azabicyclo[2.2.1]heptane borane complex To a solution of 1-azabicyclo[2.2.1]heptan-3-one (E.P. 0239309, Example 24) (3.15 g.) in water (1.0 ml) was added, without cooling, hydrochloric acid (2N, 14 ml).) followed by a solution of sodium cyanide (1.40 g.) in water (4.0 ml). After stirring at room temperature for 30 minutes the precipitate was filtered and dried in vacuo to give the cyanohydrin (3.15 g). To a chilled suspension of this cyanohydrin (3.15 g.) in dry tetrahydrofuran (50 ml) under nitrogen was added borane tetrahydrofuran complex (1.0M in tetrahydrofuran, 25 ml.) dropwise. After stirring at room temperature for 1 hour borane-tetrahydrofuran complex (1.0M in tetrahydrofuran, 50 ml, 50 mmol) was added. After heating at reflux for 1.5 hours, the reaction mixture was cooled and ethanol (50 ml) was added. Evaporation to dryness and trituration with ether gave a colourless crystalline solid (3.47 g). Recrystallisation from ethanol gave the title compound, m.p. 130°–132° C. Found: C, 53.58; H, 10.87; N, 17.97; C$_7$H$_{14}$N$_2$O.BH$_3$ requires C, 53.88; H, 10.98; N, 17.95%. $\delta_H$ (360 MHz, DMSO-d$_6$), 1.56–1.66 (1H, m, CHH), 1.74–1.84 (1H, m, CHH), 1.0–2.0 (3H, bs, BH$_3$), 2.39 (1H, d, J=4.4, CH), 2.59 (1H, d, J=8.5) and 2.65 (2H, d, J=8.7) and 2.68–2.76 (3H, m) and 2.77–2.86 (1H, m) and 3.10 (1H, d, J=8.9, four of CH$_2$N), 4.87 (1H, bs, OH). m/z 155 (M+-H).

(b) 2'-(1-Methyl-1H-indol-3-yl)spiro(3(R*), 4(R*)-1-azabicyclo[2.2.1]heptane-3,5'(4'H)-oxazole) dihydrochloride hydrate Following the method of Example 11(c), 3(R*), 4(R*)-3-aminomethyl-3-hydroxy-1-azabicyclo[2.2.1-]heptane borane complex (1.0 g, 6.4 mmol) was reacted with methyl (1-methyl-1H-indol-3-yl)imidate hydrochloride (1.2 g, 5.3 mmol), to give the title compound (1.25 g) m.p. 258°–260° C. Found: C, 54.97; H, 6.27; N, 11.30; Cl, 19.03; C$_{17}$H$_{19}$N$_3$O.2HCl.H$_2$O requires C, 54.85; H, 6.23; N, 11.29; Cl, 19.05%. $\delta_H$ (360 MHz, D$_2$O) 1.94–2.04 (1H, m, CHH), 2.32–2.44 (1H, m, CHH), 3.34–3.44 (2H, m+d, $\overline{J}$=5.0 Hz, CHHN+CH), 3.52–3.62 (2H, m+d, J=10.2, 2×CHHN+CHH), 3.75 (1H, d, J=13.8, CHH), 3.91 (1H, $\overline{d,}$ J=9.8, $\overline{CHHN}$), 3.95 (3H, s, NCH$_3$), $\overline{4.14}$ (1H, d, J=13.7, CHHN), 4.29 (1H, d, J=12.9) and 4.47 (1H, d, J=12.9, $\overline{CH_2}$N), 7.43

(1H, dt, J=7.5 and 1.5, CH), 7.49 (1H, dt, J=7.2 and 1.2, CH), 7.66 (1H, d, J=7.8, CH), 7.98 (1H, d, J=7.2, CH) and 8.26 (1H, s, CH). m/z 281 (M+).

EXAMPLE 16

2′-(1-Methyl-1H-indol-3-yl)spiro(3(S*), 4(R*)-1-azabicyclo[2.2.1]heptane-3,5′(4′H)-oxazole) 2.1 hydrochloride dihydrate (a) 3(S*), 4(R*)-3-aminomethyl-3-hydroxy-1-azabicyclo[2.2.1]heptane borane complex To a chilled solution of 1-azabicyclo[2.2.1]heptan-3-one (E.P. 0239309, Example 24) (2.0 g, 18 mmol) in water was added hydrochloric acid (2N, 9 ml, 18 mmol) followed by sodium cyanide (0.88 g, 18 mmol) in water. The precipitated cyanohydrin was filtered and dried in vacuo (1.04 g). To a suspension of the cyanohydrin in tetrahydrofuran (40 ml), under nitrogen was added borane (1.0M in tetrahydrofuran, 7.5 ml.) with ice chilling, following after 1 hour by additional borane (1.0M in tetrahydrofuran, 15 ml, 15 mmol). After 16 hours reflux the reaction mixture was cooled, and ethanol (15 ml) added. Evaporation to dryness, and crystallisation from ethanol gave the title compound (0.85 g), m.p. 147°–9° C. $\delta_H$(360 MHz, DMSO-d$_6$) 1.60 (3H, bs, BH$_3$), 1.66–1.76 (1H, m, CHH), 2.13–2.22 (1H, m, CHH), 2.40 (2H, dd, J=11.4 and 3.4, CH$_2$), 2.53 (1H, d, J=13.0) and 2.65 (1H, d, J=13.3, CH$_2$), 2.61 (1H, dd, J=9.8 and 3.4, CHHN), 2.76–2.86 (3H, m, CHHN and CH$_2$N), 2.86–2.96 (1H, m, CHHN), 4.85 (1H, bs, OH).

(b) 2′-(1-Methyl-1H-indol-3-yl)spiro(3(S*),4(R*)-1 azabicyclo[2.2.1]heptane-3,5′(4′H)-oxazole) 2.1 hydrochloride hydrate Following the method of Example 11(c), 3(S*), 4(R*)-3-aminomethyl-3-hydroxy-1-azabicyclo[2.2.1]heptane borane complex (0.35 g, 2.24 mmol) was reacted with methyl (1-methyl-1H-indol-3-yl)imidate hydrochloride to give the title compound (0.47 g), m.p. 215°–7° C. Found: C, 51.51; H, 6.36; N, 10.59; Cl, 18.98; C$_{17}$H$_{19}$N$_3$O.2.1HCl.H$_2$O requires C, 51.83; H, 6.42; N, 10.67; Cl, 18.90%; $\delta_H$ (360 MHz, D$_2$O) 2.20–2.32 (1H, m) and 2.54–2.64 (1H, m, CH$_2$), 3.34 (1H, d, J=4.0, CH), 3.48–3.76 and 3.84–3.94 (6H, each m, three of CH$_2$N), 3.95 (3H, s, NCH$_3$), 4.17 (1H, d, J=12.8) and 4.40 (1H, d, J=12.8, CH$_2$N), 7.45 (1H, t, J=6.6, CH), 7.49 (1H, t, J=5.9, CH), 7.66 (1H, d, J=8.2, CH), 7.98 (1H, d, J=7.1, CH), 8.26 (1H, s, CH). m/z 281 (M+).

EXAMPLE 17

2′-(1-Methyl-1H-indol-3-yl)spiro[1-azabicyclo[2.2.2]octane-3,5′(4′H)-oxazole]1-methyl iodide hydrate Methyl iodide (35 μl.) was added to a solution of 2′(1-methyl-1H-indol-3-yl) spiro[1-azabicyclo [2.2.2]octane-3,5′(4′H)-oxazole], (0.15 g.) in acetone, and stirred for 30 minutes at room temperature. Evaporation to dryness gave the title compound as a colourless solid (0.15 g) m.p. 198°–200° C. (dec). Found: C, 49.99; H, 5.74; N, 9.07; C$_{19}$H$_{24}$N$_3$OI.H$_2$O requires C, 50.11; H, 5.75; N, 9.23%; $\delta_H$ (360 MHz, D$_2$O), 2.02–2.26 (3H, m, CHH+CH$_2$), 2.40–2.46 (1H, m, CH), 2.46–2.58 (1H, m, CHH), 3.11 (3H, s, N—CH$_3$), 3.38–3.48 (1H, m, CHHN), 3.48–3.62 (1H, m, CHHN), 3.62–3.72 (2H, m, CH$_2$), 3.80 (1H, d, J=14.5, CHHN), 3.89 (3H, s, NCH$_3$), 3.92 (1H, d, J=14.5, CHH), 3.95 (1H, d, J=14.4, CHHN), 4.23 (1H, d, J=14.6, CHHN), 7.36 (1H, t, J=6.9, CH), 7.43 (1H, t, J=6.8, CH), 7.60 (1H, d, J=8.2, CH), 7.96 (1H, s, CH), 8.0 (1H, d, J=7.9, CH). m/z 310 (M+).

EXAMPLE 18

[2′-(Benzo[b]thiophen-3-yl)-]spiro(1-azabicyclo[2.2.2]octane-3,5′(4′H)-oxazole) dihydrochloride hydrate (a) Methyl(benzo[b]thiophen-3-yl)imidate hydrochloride Benzo[b]thiophen-3-carbonitrile (700 mg) was dissolved in dry methanol (25 ml), and the resulting solution cooled to 10° C. under a dry nitrogen atmosphere. Dry hydrogen chloride gas was passed through the chilled solution for 40 minutes, and the resulting red solution allowed to stand at room temperature overnight. Removal of solvent under reduced pressure and recrystallisation from methanol/ether afforded the title compound as white needles (810 mg), m.p. 197°–200° C. $\delta_H$ (360 MHz, DMSO-d$_6$) 4.35 (3H, s, OCH$_3$), 7.53 (2H, m, H-5,6), 8.19 (2H, m, H-4, 7 ) 8.41 (1H, s, H-2); m/z 191(M+, 70%) 160(100), 133(30), 89(40).

(b) [2′-(Benzo[b]thiophen-3-yl)-]spiro(1-azabicyclo[2.2.2]octane)-3,5′(4′H)-oxazole) hydrochloride 3-Aminomethyl-3-hydroxy-1-azabicyclo[2.2.2]octane (420 mg) in dry methanol (50 ml) was added to a solution of methyl (benzo[b]thiophen-3-yl)imidate hydrochloride (500 mg) in dry methanol (50 ml) stirring at room temperature under a dry nitrogen atmosphere. The mixture was heated at reflux overnight, cooled to room temperature and the solvent removed under reduced pressure. The residue was taken up in 2N hydrochloric acid (50 ml), extracted with dichloromethane (6×50 ml), basified to pH 12 (0.88 NH$_4$OH), extracted with dichloromethane (6×50 ml), and the final organic extract dried (MgSO$_4$). Removal of solvent under reduced pressure and chromatography on silica gel (ether/hexane 1:4) afforded a colourless oil (400 mg). Treatment with saturated ethereal hydrogen chloride and recrystallisation from methanol afforded the title compound as white needles (270 mg), m.p. 167°–70° C. Found: C, 49.62; H, 5.96; N, 6.80; C$_{17}$H$_{24.2}$N$_2$O$_{3.1}$Cl$_2$S requires C, 49.90; H, 5.96; N, 6.84%; $\delta_H$ (360 MHz, DMSO-d$_6$) 1.93 (3H, brm, CH$_2$CH$_2$N), 2.26 (1H, brm, CH$_2$CH$_2$N), 2.36 (1H, brm, CHCH$_2$CH$_2$N) 3.16–3.49 (2H, brm, CH$_2$CH$_2$N), 4.12 (2H, d, J=15.0 Hz, C=NCH$_2$), 4.29 (2H, d, J=15.0 Hz C=N-CH$_2$), 7.52 (2H, m, H-5,6), 8.12 (1H, dd, J=7.0, 1.0 Hz, H-4), 8.59 (1H, dd, J=7.0, 1.0 Hz), H-7), 8.91 (1H, s, H-2); m/z 298(M+, 25), 157(40), 139(30), 96(100), 82(60), 69(35).

EXAMPLE 19

2′(1-Propyn-2-yl-1H-indol-3-yl)spiro[1-azabicyclo[2.2.2]octane-3,5′(4′H)-oxazole] dihydrochloride sesquihydrate (a) 2′-(1H-Indol-3-yl)spiro[1-azabicyclo[2.2.2]octane-3,5′(4′H)-oxazole]-borane complex To a solution of 3-aminomethyl-3-hydroxy-1-azabicyclo[2.2.2]octane-borane complex (10.0 g.) in methanol (220 ml) was added dropwise a solution of methyl (1H-indol-3-yl)imidate hydrochloride (10.9 g.) in methanol (1000 ml). The reaction mixture was stirred at room temperature for 24 hours under nitrogen, then stirred at 50° C. for a further 12 hours. The mixture was allowed to cool and basified with 0.88M ammonium hydroxide solution. The mixture was evaporated to dryness. The residue was purified by column chromatography on silica, eluting with dichloromethane/methanol 9:1, to give (14.2 g), m.p. 262°-264° C. $\delta_H$ (360 MHz, DMSO-d$_6$) 1.1-1.7 (3H, s, BH$_3$), 1.69-1.75 (3H, m) and 2.04 (1H, s, two CH$_2$), 2.14-2.16 (1H, m, CH), 2.86-2.95 (2H, m) and 3.00-3.05 (2H, t, two N—CH$_2$), 3.08-3.11 (1H, d, J=14.2) and 3.12-3.17 (1H, d, J=14.2, N—CH$_2$), 3.80-3.84 (1H, d, J=14.8) and 4.03-4.07 (1Hd, d, J=14.7, CH$_2$), 7.18-7.25 (2H, m, two CH), 7.44 (1H, dd) and 7.9 (1H, d, two CH), 8.04 (1H, d, CH), 11.69 (1H, s, NH); m/z 281(M+ free base, 20), 271(100%).

(b)
2'(1-Propyn-2-yl-1H-indol-3-yl)spiro[1-azabicyclo[2.2.2]octane-3,5'-(4'H)-oxazole]dihydrochloride sesquihydrate To a solution of the aforementioned borane complex (0.5 g.) in tetrahydrofuran (40 ml) under nitrogen was added sodium hydride (0.09 g.). After stirring at room temperature for 30 minutes propargyl bromide (0.16 ml.) was added. After stirring at room temperature for 12 hours the mixture was evaporated to dryness. The residue was dissolved in methanol and treated with methanolic hydrogen chloride. After heating at 60° C. for 24 hours the mixture was evaporated to dryness. The residue was dissolved in water and washed with dichloromethane. The aqueous solution was basified with 0.88M ammonium hydroxide solution. This solution was then extracted with dichloromethane (3×100 ml). The organic extracts were dried (MgSO$_4$) and evaporated at reduced pressure. The residue was dissolved in methanol and treated with ethereal hydrogen chloride to give the title compound as a colourless crystalline solid (0.22 g), m.p. 200°-220° C. Found: C, 57.26; H, 6.21; N, 10.05; C$_{20}$H$_{21}$N$_3$O.2HCl.1.5H$_2$O requires C, 57.27; H, 6.21; N, 10.02%; $\delta_H$ (360 MHz, D$_2$O) 2.09-2.28 (3H, m), 2.50-2.52 (1H, m, two CH$_2$), 2.74 (1H, m, CH), 2.97-2.99 (1H, t, CH), 3.38-3.46 (2H, m), 3.55-3.66 (2H, m, two N—CH$_2$), 3.83-3.87 (1H, dd), 4.09-4.13 (1H, d, N—CH$_2$), 4.19-4.23 (1H, d), 4.48-4.51 (1H, d, CH$_2$), 5.18-5.19 (2H, d, N—CH$_2$), 7.45-7.55 (2H, m, two CH), 7.76-7.78 (1H, dd), 7.94-7.97 (1H, dd, two CH) and 8.54 (1H, s, CH); m/z 319 (M+, 15), 225 (100).

EXAMPLE 20

2'(1-Propen-2-yl-1H-indol-3-yl)spiro[1-azabicyclo[2.2.2]octane-3,5'(4'H)-oxazole]dihydrochloride dihydrate To a solution of 2'-(1H-indol-3-yl)spiro[1-azabicyclo[2.2.2]-octane-3,5'(4'H)-oxazole] borane complex (0.5 g.) in tetrahydrofuran (40 ml) under nitrogen was added sodium hydride (55% suspension in oil, 0.09 g.). After stirring at room temperature for 30 minutes, allyl bromide (0.24 g.) was added. After stirring at room temperature for 24 hours the mixture was evaporated to dryness. The residue was dissolved in methanol and treated with methanolic hydrogen chloride. After heating at 60° C. for 36 hours the mixture was evaporated to dryness. The residue was dissolved in water and washed with dichloromethane. The aqueous solution was basified with 0.88M ammonium hydroxide solution. This solution was extracted with dichloromethane (3×100 ml). The organic extracts were dried (MgSO$_4$) and evaporated. The residue was purified by column chromatography on silica, eluting with dichloromethane/methanol 9:1. The product was dissolved in methanol and treated with ethereal hydrogen chloride, and evaporated. Recrystallisation from propan-2-ol gave the title compound as a white crystalline solid (0.2 g), m.p. 215°-217° C. Found: C, 55.70; H, 6.54; N, 9.67; C$_{20}$H$_{23}$N$_3$O.2HCl.2H$_2$O requires C, 55.87; H, 6.79; N, 9.76%; $\delta_H$(360 MHz, D$_2$O) 2.00-2.30 (3H, m), 2.46-2.54 (1H, m, two CH$_2$), 2.63 (1H, s, CH), 3.38-3.44 (2H, m), 3.54-3.62 (2H, m, two CH$_2$), 3.75-3.79 (1H, d), 4.00-4.04 (1H, d, CH$_2$), 4.10-4.14 (1H, d, J=13), 4.39-4.43 (1H, d, J=13, CH$_2$), 4.95-4.96 (2H, d, CH$_2$), 5.04-5.09 (1H, d), 5.26-5.29 (1H, d, CH$_2$), 6.00-6.18 (1H, m, CH), 7.42-7.46 (2H, m, two CH), 7.64-7.66 (1H, d), 7.97-7.99 (1H, d, two CH) and 8.31 (1H, s, CH); m/z 329 (M+, 10%), 96 (100).

EXAMPLE 21

[2'-(5-Amino-1-methyl-1H-indol-3-yl)-]spiro(1-azabicyclo[2.2.2]octane-3,5'(4'H)-oxazole) hydrochloride (a)
[2'-(5-Amino-1-methyl-1H-indol-3-yl)-]spiro(1-azabicyclo[2.2.2]octane-3,5'(4'H)-oxazole)-borane complex

[2'-(5-Nitro-1-methyl-indol-1H-3-yl)-]spiro(1-azabicyclo[2.2.2]octane-3,5'(4'H)-oxazole) borane complex (500 mg) was suspended in ethyl acetate (50 ml) and hydrogenated over 10% Pd/C (50 mg) for six hours at atmospheric pressure. The catalyst was filtered and the solvent removed under reduced pressure. The residue was chromatographed on silica gel using dichloromethane/ammonium hydroxide 90/10/1 as eluant to afford the title compound (140 mg), m.p. 225°-230° C.; $\delta_H$ (360 MHz, CDCl$_3$) 1.81 (3H, brm, CH$_2$CH$_2$N), 2.14(1H, brm, CHCH$_2$CH$_2$N), 2.29 (1H, brm, CH$_2$CH$_2$N), 2.95-3.2 (6H, brm, CH$_2$CH$_2$N), 3.76 (3H, s, N-CH$_3$), 3.81 (1H, d, J=14.4 Hz, C=N-CH$_2$), 4.16 (1H, d, J=14.4 Hz, C=N-CH$_2$), 6.73 (1H, dd, J=10.8 Hz, H-6), 7.13 (1H, d, J=10.8 Hz, H-7), 7.41 (1H, d, J=1.0 Hz, H-4), 7.50 (1H, s, H-2); m/z 325 (M+, 10), 311 (25), 185 (40), 93 (100), 75 (40).

(b) [2'-(5-Amino-1-methyl-1H-indol-3-yl)-]spiro (1-azabicyclo[2.2.2]octane-3,5'(4'H)-oxazole) trihydrochloride hydrate 2'-(5-Amino-1-methyl-1H-indole-3-yl) spiro[1-azabicyclo[2.2.2]octane-3,5'(4'H)-oxazole] borane complex (140 mg) was dissolved in methanol (50 ml) previously saturated with hydrogen chloride gas. The resulting solution was heated at reflux for one hour, cooled to room temperature and the solvent removed. The residue was recrystallised from isopropanol to give the title compound (140 mg), m.p. 260° C. (dec); Found: C, 48.30; H, 6.26; N, 12.36; C$_{18}$H$_{28}$N$_4$O$_{2.5}$Cl$_3$ requires C, 48.38; H, 6.31; N, 12.54%: $\delta_H$(360 MHz, D$_2$O) 2.17 (3H, bm, CH$_2$CH$_2$N), 2.50 (1H, bm, CH$_2$CH$_2$N), 2.73 (1H, bm, CHCH$_2$CH$_2$N), 3.45 (2H, bt, J=9.5 Hz, CH$_2$CH$_2$N), 3.64 (2H, bt, J=9.5 Hz, CH$_2$CH$_2$N), 3.85 (1H, d, J=12.0 Hz, CH$_2$CH$_2$N), 3.98 (3H, s, N-CH$_3$), 4. (1H, d, J=12.0 Hz, CH$_2$CH$_2$N), 4.20 (1H, d, J=10.0 Hz, C=N-CH$_2$), 4.50 (1H, d, J=10.0 Hz, C=N-CH$_2$), 7.40 (1H, dd, J=11.0, 1.0 Hz, H-6), 7.75 (1H, d, J=11.0 Hz, H-7), 7.90 (1H, d, J=1.0 Hz, H-4), 8.41 (1H, s, H-2); m/z 310 (M+, 100) 171 (30), 139 (50), 111 (10), 96 (80), 82 (35), 69 (20).

EXAMPLE 22

[2'-(2-Iodo-1-methyl-1H-indol-3-yl)-]spiro(1-azabicyclo[2.2.2]octane-3,5'(4'H)-oxazole) dihydrochloride t-Butyllithium (2 ml of a 1.7M soln in hexane) was added dropwise to a stirred solution of [2'-(1-methyl- 1H-indol-3-yl)-]spiro(1-azabicyclo[2.2.2]octane-3,5'(4'H)-oxazole) (0.5 g, 1.7 mmol) in tetrahydrofuran (20 ml) at −78° C. under a nitrogen atmosphere. After stirring for 1 hr at −78° C. a solution of iodine (0.5 g in 10 ml THF) was added dropwise until the colour persisted. The mixture was then allowed to warm to room temperature, diluted with water (100 ml), extracted with chloroform (2×100 ml), and dried ($Na_2SO_4$). The solvent was removed at reduced pressure to afford an off-white solid (0.6 g). This was further purified by treatment with a solution of hydrogen chloride in methanol (excess) and evaporation. Recrystallisation from methanol afforded a white crystalline solid (0.5 g); m.p 188° C. (dec). Found: C, 40.77; H, 4.94; N, 7.92; $C_{18}H_{20}N_3OI$ requires C, 40.50; H, 5.17; N, 7.72%: $\delta_H$ (360 MHz, $D_2O$) 2.1–2.3 (3H, m, $CH_2CHH$), 2.6 (1H, m, $CHH$), 2.76 (1H, m, CH), 3.46–3.72 (4H, m, 2×$CH_2N$), 3.84 (3H, s, NMe), 3.93 (1H, d, J=12 Hz, CHHN), 4.12 (1H, a, J=12 Hz, CHHN) 4.25 (1H, d, J=13 Hz, CHHN), 4.52 (1H, d, J=13 Hz, CHHN), 7.4–7.47 (2H, m, H-5, H-6), 7.61 (1H, d, J=7 Hz, H-7), 7.81 (1H, d, J=7 Hz, H-4); m/z (M+, free base, 30%), 295(20), 139(75), 96(100).

EXAMPLE 23

[2'-(1H-Indazole-3-yl)-]spiro(1-azabicyclo[2.2.2]octane-3,5'(4'H)-oxazole) hydrochloride Anhydrous hydrogen chloride was passed through a solution of indazole-3-carbonitrile (2.3 g) in anhydrous methanol (50 ml) for one hour. The solvent was then removed under reduced pressure and the residue redissolved in anhydrous methanol (50 ml). A solution of 3-aminomethyl-3-hydroxy-1-azabicyclo[2.2.2]octane (3.51 g) in anhydrous methanol (50 ml) was added over a period of one hour. The solution was then heated at reflux for 18 hours, cooled to room temperature and evaporated to dryness. The residue was taken up in 2N hydrochloric acid (100 ml), extracted with dichloromethane (4×100 ml), basified to pH 12 with 0.88 ammonium hydroxide solution, and extracted with dichloromethane (6×100 ml). The final organic extracts were washed with ether (100 ml) dried ($MgSO_4$) and the solvent removed to give a white solid. Treatment with excess ethereal hydrogen chloride and recrystallisation from ethanol gave the title compound (950 mg), m.p. 187°–189° C. Found: C, 52.73; H, 6.04; N, 14.86; $C_{16}H_{20}N_4OCl_2$. $\frac{3}{8}H_2O$. requires C, 52.72; H, 6.16; N, 14.63%; $\delta_H$ (360 MHz, DMSO) 1.95 (3H, bm, $CH_2CH_2N$), 2.36 (1H, bm, $CH_2CH_2N$), 2.54 (1H, bm, $CHCH_2CH_2N$), 3.24 (3H, bm, $CH_2CH_2N$), 3.41 (3H, bm, $CH_2CH_2N$), 4.22 (1H, d, J=14.4 Hz, C=N-$CH_2$,), 4.39 (1H, d, J=14.4 Hz, C=N-$CH_2$), 7.40 (1H, d, J=7.2 Hz, H-6), 7.52 (1H, t, J=7.2 Hz, H-5), 7.71 (1H, d, J=7.2 Hz, H-6), 8.15 (1H, d, J=7.2 Hz, H-7), 8.85 (1H, bs, H-1); m/z 282 (M+, 40), 145 (20), 121 (15), 108 (10), 97 (80), 96 (100), 82 (50), 69 (30).

EXAMPLE 24

2'-(1-Ethyl-1H-indol-3-yl)-spiro[1-azabicyclo[2.2.2]octane-3,5(4'H)-oxazole] dihydrochloride dihydrate To a solution of 2'-(1H-indol-3-yl)spiro[1-azabicyclo[2.2.2]-octane-3,5'(4'H)-oxazole] borane complex (1.0 g, 3.4 mmol) in tetrahydrofuran (40 ml) under nitrogen was added sodium hydride (55% suspension in oil, 0.18 g,). After stirring at room temperature for 45 minutes, ethyl iodide (0.64 g,) was added. After stirring at room temperature for 8 hours the mixture was evaporated to dryness. The residue was dissolved in methanol and treated with methanolic hydrogen chloride. After heating at 60° C. for 3 hours the mixture was evaporated. The residue was dissolved in water and washed with dichloromethane. The aqueous solution was basified with 0.88M ammonium hydroxide. This solution was then extracted with dichloromethane (3×100 ml). The organic extracts were dried ($MgSO_4$) and evaporated. The residue was dissolved in methanol and treated with ethereal hydrogen chloride and ether to give a brown solid. The solid was dissolved in the minimum of hot propan-2-ol and stirred with charcoal. The solution was filtered and allowed to cool to give the title compound as a cream crystalline solid (0.24 g), m.p. 194°–196° C.; $\delta_H$ (360 MHz, $D_2O$) 1.51–1.55 (3H, t, J=7.3, $CH_3$), 2.08–2.27 (3H, m), 2.78 (1H, s, two $CH_2$), 2.53 (1H, m, CH), 3.44–3.46 (2H, t), 3.61–3.66 (2H, m, two $CH_2$), 3.86–3.90 (1H, d, J=15.1 Hz), 4.12–4.16 (1H, d, J=15.1 Hz, $CH_2$), 4.21–4.25 (1H, d, J=11.9 Hz), 4.50–4.53 (1H, d, J=11.9 Hz, $CH_2$), 4.36–4.42 (2H, q, J=7.3 Hz, $CH_2$); m/z 309 (M+).

EXAMPLE 25

(a)

2'-(5-Nitro-1-methyl-indol-3-yl)-]spiro(1-azabicyclo[2.2.2]octane-3,5'(4'H)-oxazole)-borane complex 2'-(5-Nitro-1H-indol-3-yl)-]spiro(1-azabicyclo[2.2.2]octane-3,5'(4'H)-oxazole) borane complex (3 g) was suspended in dry tetrahydrofuran (80 ml) under a dry nitrogen atmosphere. Sodium hydride (211 mg of 55% dispersion in oil) was added and the solution stirred until the evolution of hydrogen ceased. Methyl iodide (1.25 g) was added dropwise over a period of ten minutes, and the resulting mixture stirred for four hours at room temperature. The bright yellow precipitate was filtered and recrystallised from absolute ethanol to afford the title compound (2.7 g), m.p. 195°–200° C.; $\delta_H$ (360 MHz, DMSO-$d_6$) 1.76 (4H, brm, $CH_2CH_2N$), 2.07 (1H, brm, $CHCH_2CH_2N$), 2.9–3.1 (4H, brm $CH_2CH_2$), 3.6 (2H, brm, $CH_2CH_2N$), 3.89 (1H, d, J=15.4 Hz, $CH_2$—C—O), 3.92 (3H, s, N-$CH_3$), 4.10 (1H, d, J=15.4 Hz, $CH_2$—C—O), 7.76 (1H, d, J=11.6 Hz, H-7), 8.14 (1H, dd, J=11.6, 1.0 Hz, H-6), 8.21 (1H, s, H-2), 8.96 (1H, d, J=1.0 Hz, H-4); m/z (M+, 80% free base), 340 (80), 310 (30), 250 (15), 191 (30), 154 (95), 132 (20), 96 (100), 82 (40).

(b)

2'-(5-Nitro-1-methyl-indol-3-yl)-]spiro(1-azabicyclo[2.2.2]octane-3,5'(4'H)oxazole) tetrahydrochloride 2'-(5-Nitro-1-methyl-indol-3-yl)-]spiro(1-azabicyclo[2.2.2]octane-3,5'(4'H)-oxazole) borane complex (250 mg) was suspended in absolute methanol saturated with HCl gas with vigorous stirring. The solution was warmed to 55° C. for three hours, cooled to room temperature and the solvent removed under reduced pressure. The residue was recrystallised from absolute ethanol to give the title compound (100 mg), m.p. 245°–250° C. Found: C, 44.76; H, 5.16; N, 11.54; $C_{18}H_{24}N_4O_3Cl_4$ requires C, 44.46; H, 4.98; N, 11.52%; $\delta_H$ (360 MHz, $D_2O$) 2.10 (3H, brm, $CH_2CH_2N$), 2.51 (1H, brm, $CH_2CH_2N$), 2.75 (1H, brm, $CHCH_2CH_2N$), 3.46 (2H, brm, $CH_2CH_2N$), 3.64 (2H, brm, $CH_2CH_2N$), 3.85 (2H, d, J=14.4 Hz, $R_2CCH_2N$), 3.97 (3H, s, N-$CH_3$), 4.12 (2H, d, J=14.4 Hz, $R_2C$-$CH_2$-N), 4.23 (2H, d, J=10.8 Hz, C=N-$CH_2$), 4.78 (2H, d, J=10.8 Hz, C=N-$CH_2$), 7.63 (1H, d, J=7.2 Hz, H-7), 8.16 (1H, dd, J=7.2, 1.0

Hz, H-6), 8.44 (1H, s, H-2), 8.6 (1H, d, J=1.0 Hz, H-4); m/z (M+, 50%, free base) 340 (50), 310 (10), 203 (10), 157 (15), 139 (50), 96 (100), 82 (45).

EXAMPLE 26

[2'-(5-Methoxy-1-methyl-1H-indole-3-yl)-]spiro(1-azabicyclo[2.2.2]octane-3,5'(4'H)-oxazole) trihydrochloride (a) 5-Methoxy-1H-indole-3-carboxylate Trifluoroacetic anhydride (15 ml) was added to a chilled (0° C.) solution of 5-methoxy-1H-indole (10 g) in dry dimethylformamide (200 ml) under a dry $N_2$ atmosphere. The solution was allowed to warm to room temperature overnight, poured into water (500 ml), and the pink solid was filtered. This was re-suspended in water (300 ml), sodium hydroxide (30 g) was added and the solution heated at reflux for three hours. The solution was then cooled to 10° C., neutralised to pH2 with conc HCl, solid isolated by filtration and dried in vacuo to afford the title compound (4.4 g), m.p. 215°–220° C.; $\delta_H$ (360 MHz, DMSO-$d_6$) 3.78 (3H, s, O$\underline{CH_3}$), 6.81 (1H, dd, J=5.0, 1.0 Hz, H-6), 7.35 (1H, d, J=5.0 Hz, H-7), 7.49 (1H, d, J=1.0 Hz, H-4), 7.93 (1H, s, H-2); m/z 191 (M+, 70), 147 (80), 104 (100), 77 (40).

(b) 5-Methoxy-1H-indole-3-carboxamide

Oxalyl chloride (3.0 g) was added dropwise to a stirred solution of 5-methoxy-1H-indole-3-carboxylate (4.4 g) in tetrahydrofuran under a dry $N_2$ atmosphere. The solution was stirred at room temperature overnight, the solvent removed under reduced pressure, and the residue redissolved in dry 1,2-dichloroethane. Anhydrous ammonia was passed through the solution for 1.5 hours, and the solution stirred for a further three hours at room temperature. The solution was then filtered to afford the title compound as a pale red powder (6.1 g), m.p. 260° C. (dec); $\delta_H$ (360 MHz, DMSO-$d_6$) 3.76 (3H, s, O$\underline{CH_3}$), 6.75 (1H, dd, J=6.5, 1.0 Hz, H-6), 7.30 (1H, d, J=6.5 Hz, H-7), 7.49 (1H, d, J=1.0 Hz, H-4), 8.15 (1H, s, H-2) m/z 190(M+, 100), 147(30), 91(55).

(c) 5-Methoxy-1H-indole-3-carbonitrile

5-Methoxy-1H-indole-3-carboxamide (6.1 g) was treated with refluxing POCl$_3$ (65 ml) for ten minutes. Excess POCl$_3$ was removed under high vacuum (0.1 mmHg) and the residue quenched with water/0.88 NH$_4$OH 1:1 (100 ml). The resulting solution was extracted with CHCl$_3$ (4×100 ml), treated with charcoal (10 g), dried (MgSO$_4$), filtered and the solvent removed to afford a brown solid. Recrystallisation from hexane afforded the title compound as pale brown needles (3.3 g), m.p. 147° C.; $\delta_H$ (360 MHz, CDCl$_3$) 3.86 (3H, s, O$\underline{CH_3}$), 6.90 (1H, dd, J=7.5, 1.0 Hz, H-6), 7.13 (1H, d, J=1.0 Hz, H-4), 7.36 (1H, d, J=7.5 Hz, H-7), 7.67 (1H, s, H-2).

(d) 5-Methoxy-1-methyl-1H-indole-3-carbonitrile

A solution of 5-methoxy-1H-indole-3-carbonitrile (550 mg) in dry tetrahydrofuran (50 ml) was treated with NaH (152 mg of a 55% dispersion in oil). The solution was stirred under a dry nitrogen atmosphere until the evolution of hydrogen ceased. Methyl iodide (0.45 mg) was then added and the reaction allowed to stir at room temperature for one hour. The solvent was then removed under reduced pressure and the residue taken up in dichloromethane (50 ml), washed with water (2×25 ml), dried (MgSO$_4$), filtered, and evaporated to dryness under reduced pressure. The residue was recrystallised from absolute ethanol to afford the title compound as white prisms (480 mg); m.p. 105°–108° C.; $\delta_H$ (360 MHz, CDCl$_3$) 3.84 (3H, s, O$\underline{CH_3}$), 3.87 (3H, s, N$\underline{CH_3}$), 6.98 (1H, dd, J=7.5, 1.0 Hz, $\overline{\text{H-6}}$), 7.12 (1H, d, J=1.0 Hz, H-4), 7.31 (1H, d, J=7.5 Hz, H-7), 7.61 (1H, s, H-2); m/z 186 (M+100), 171 (90), 143 (80), 116 (20), 101 (15), 89 (15).

(e) Methyl(5-methoxy-1-methyl-1H-indol-3-yl) imidate hydrochloride

Anhydrous hydrogen chloride gas was passed through a solution of 5-methoxy-1-methyl-1H-indole-3-carbonitrile (100 mg) in dry methanol (50 ml) for 1.5 hours. The solution was cooled to 0° C. and filtered to afford the title compound as pink needles (260 mg), m.p. 220° C. (dec); $\delta_H$ (360 MHz, CDCl$_3$) 3.79 (3H, s, N$\underline{CH_3}$), 3.89 (6H, s, 2×O$\underline{CH_3}$), 6.93 (1H, dd, J=7.5, 1.0 Hz, $\overline{\text{H-6}}$), 7.22 (1H, d, J=7.5 Hz, H-7), 7.65 (1H, d, J=1.0 Hz, H-4), 7.70 (1H, s, H-2); m/z 219 (M++1, 100), 188 (60), 145 (20), 117 (10).

(f) [2'-(5-Methoxy-1-methyl-1H-indol-3-yl)-]spiro(1-azabicyclo[2.2.2]octane-3,5'(4'H)-oxazole borane complex 3-Aminomethyl-3-hydroxy-1-azabicyclo[2.2.2]octane borane complex (262 mg) in dry methanol (50 ml) was added over thirty minutes to a stirred solution of methyl (5-methoxy-1-methyl-1H-indol-3-yl)imidate hydrochloride (260 mg) in dry methanol (100 ml) under a dry nitrogen atmosphere. The mixture was warmed at reflux for six hours, cooled to room temperature, solvent removed under reduced pressure, and the residue chromatographed on silica gel using 4% methanol/dichloromethane to afford the title compound as a white solid (260 mg), m.p. 198° C.; $\delta_H$ (CDCl$_3$) 1.77 (3H, brm, C$\underline{H_2}$CH$_2$N), 2.15 (1H, brm, C$\underline{H}$CH$_2$CH$_2$N), 2.26 (1H, brm, C$\underline{H_2}$CH$_2$N), 2.98 (2H, brm, CH$_2$C$\underline{H_2}$N), 3.08 (1H, d, J=14.0 1 Hz, CH—C—C$\underline{H_2}$N), 3.13 (2H, brm, C$\underline{H_2}$CH$_2$N), 3.39 (1H, d, J=14.0 Hz, CH—C—C$\underline{H_2}$N), 3.81 (3H, s, O$\underline{CH_3}$), 3.85 (1H, d, J=13.5 Hz, C=N—C$\underline{H_2}$), 3.89 (3H, s, N$\underline{CH_3}$), 4.17 (1H, d, J=13.5 Hz, C=N—C$\underline{H_2}$), 6.95 (1H, dd, J=7.0, 1.0 Hz, H-6), 7.24 (1H, d, J=7.0 Hz, H-7), 7.55 (1H, s, H-2), 7.61 (1H, d, J=1.0 Hz, H-4); m/z (M+ free base, 25%;) 325 (20), 205 (30, 139 (15), 83 (100).

(g) [2'-(5-Methoxy-1-methyl-1H-indol-3-yl)-]spiro(1-azabicyclo[2.2.2]octane-3,5'(4'H)-oxazole trihydrochloride

[2'-(5-Methoxy-1-methyl-1H-indol-3-yl)-]spiro(1-azabicyclo[2.2.2]octane-3',5'(4'H)-oxazole) borane complex (260 mg) was dissolved in methanol (50 ml) previously saturated with HCl gas. The solution was warmed to 55° C. for four hours, cooled to room temperature and the solvent removed under reduced pressure. The residue was recrystallised from dry ethanol to afford the title compound as white needles (210 mg), m.p. 210°–214° C. Found C, 49.67; H, 6.46; N, 9.39; $C_{19}H_{26}N_3O_2Cl_3.2.5H_2O$ requires C, 49.46; H, 6.22; N, 9.12%; $\delta_H$ (360 MHz, D$_2$O) 2.09 (4H, brm, CHC$\underline{H_2}$CH$_2$N), 2.71 (1H, brm, C$\underline{H}$CH$_2$CH$_2$N), 3.58 (4H, brm, CH$_2$C$\underline{H_2}$N), 3.87 (1H, d, J=11.0 Hz, CH—C—C$\underline{H_2}$N), 3.91 (6H, s, O$\underline{CH_3}$, N$\underline{CH_3}$), 4.06 (1H, d, J=11.0 Hz, CH—C—C$\underline{H_2}$N), 4.15 (1H, d, J=13.0 Hz, C=N—CH₂), 4.45 (1H, d, J=13.0 Hz, C=N—CH₂), 7.14 (1H, dd, J=7.0, 1.0 Hz, H-6), 7.35 (1H, d, J=1.0 Hz, H-4), 7.56 (1H, d, J=7.0 Hz, H-7), 8.26 (1H, s, H-2); m/z 325 (M+, 40), 188 (30), 139 (40), 96 (100).

EXAMPLE 27

[2'-(5-Hydroxy-1-methyl-1H-indol-3-yl)-]spiro(1-azabicyclo[2.2.2]octane-1H-3,5'(4'H)-oxazole) hydrochloride (a)

[2'-(5-Methoxy-1-methyl-1H-indol-3-yl)-]spiro(1-azabicyclo[2.2.2]octane-3,5'(4'H)-oxazole)

[2'-(5-Methoxy-1-methyl-1H-indol-3-yl)-]spiro(1-azabicyclo[2.2.2]octane)-3,5'(4'H)-oxazole) borane complex (1.9 g) was dissolved in methanol (100 ml) previously saturated with hydrogen chloride gas. The solution was warmed to 55° C. for three hours, cooled to room temperature, and the residue taken up in water (50 ml). The aqueous solution was basified with 0.88 NH₄OH to pH 11, extracted with dichloromethane (4×50 ml), and dried (MgSO₄); the solvent was then removed under reduced pressure. Purification by chromatography on silica gel using dichloromethane/methanol (99:1) as eluant offorded the title compound as a colourless oil (1.1 g); δ$_H$ (360 MHz, CDCl₃) 1.54 (1H brm, CH₂CH₂N), 1.60 (2H brm, CH₂CH₂N) 1.68 (1H, brm, CHCH₂CH₂N), 2.21 (1H, brm, CH₂CH₂N) 2.84 (2H, brm, CH₂CH₂N), 2.84 (1H, d, J=10.8 Hz CH—C—CH₂N), 3.1 (2H, brm, CH₂CH₂N), 3.3 (1H, d, J=10.8 Hz CH—C—CH₂N) 3.70 (1H, d, J=14.5 Hz C=N CH₂), 3.79 (3H, s, OCH₃), 3.89 (3H, s, NCH₃) 4.17 (1H, d, J=14.5 Hz C=N CH₂), 6.92 (1H, dd, J=10, 10 Hz, H-6), 7.21 (1H, d, J=10 Hz, H-7), 7.57 (1H, s, H-2), 7.66 (1H, d, J=10 Hz H-4); m/z 325 (M+, 60%), 188(25), 139(60), 96(100), 82(50).

(b)

[2'-(5-Hydroxy-1-methyl-1H-indol-3-yl)-]spiro(1-azabicyclo[2.2.2]octane-3,5'(4'H)-oxazole) trihydrochloride hydrate

[2'-(Methoxy-1-methyl-1H-indol-3-yl)-]spiro(1-azabicyclo[2.2.2]octane-3,5'(4'H)-oxazole) (160 mg) was dissolved in dry dichloromethane (50 ml) and cooled to −78° C. under a dry nitrogen atmosphere. Boron tribromide (0.63 g) was added and the resulting solution allowed to warm to room temperature over three hours. The reaction was then quenched with crushed ice (10 g), basified to pH 7.5 with 0.88 NH₄OH, extracted with dichloromethane (2×100 ml) and the organic extracts dried (MgSO₄). Filtration and removal of solvent under reduced pressure afforded a yellow gum. Treatment with excess ethereal hydrogen chloride, filtration and recrystallisation of the recovered solid afforded the title compound as white needles (120 mg); m.p. 215°-220° C. (dec). Found: C, 50.99; H, 6.06; N, 9.50; $C_{18}H_{21}N_3O_2$.3HCl 0.3H₂O requires C, 50.73; H, 5.81; N, 9.86 δH (360 MHz, D₂O) 2.21 (3H, brm, CH₂CH₂N), 2.48 (1H, brm, CH₂CH₂N), 2.72 (brm CH₂CH₂CH₂N) 3.45 (2H, brm, CH₂CH₂N), 3.65 (2H, brm, CH₂CH₂N), 3.84 (1H, J=14.0 Hz, CH—C—CH₂N), 3.90 (3H, s, NCH₃), 4.10 (1H, d, J=14.0 Hz, CH—C—CH₂N) 4.18 (1H, d, J=14.5 Hz, C=N-CH₂), 4.45 (1H, d, J=14.5 Hz, C=N-CH₂) 7.02 (1H, dd, J=10, 10 Hz, H-6), 7.29 (1H, d, J=10 Hz H-4), 7.50 (1H, d, J=10 Hz, H-7), 8.24 (1H, s, H-2); m/z 311(M+, free base, 40%), 174(20), 156(25), 139(40), 96(100), 82(60).

EXAMPLE 28

[2'-(1,5-Dimethyl-1H-indol-3-yl)-]spiro(1-azabicyclo[2.2.2]octane-3,5'(4'H)-oxazole) 2.1 hydrochloride hydrate (a) Methyl (1,5-Dimethyl-1H-indol-3-yl) imidate hydrochloride Dry hydrogen chloride gas was bubbled through a water cooled solution of 1,5-dimethyl-1H-indole-3-nitrile (0.3 g, 1.8 mmol) in methanol (30 ml) until the solution was saturated. After standing for 3 days, evaporation to dryness and trituration with ether, the title compound was obtained as colourless crystals (0.38 g); m.p. 128°-130° C.; δ$_H$ (360 MHz, DMSO-d₆), 2.45 (3H, s, CH₃), 3.91 (3H, s, N-CH₃), 4.30 (3H, s, OCH₃), 7.21 (1H, d, J=8.4, CH), 7.55 (1H, d, J=8.4, CH), 7.74 (1H, s, CH), 8.76 (1H, s, CH), 10.28 (1H, s, NH), 11.16 (1H, s, NH); m/z 202 M+.

(b)

[2'-(1,5-Dimethyl-1H-indol-3-yl)-]spiro(1-azabicyclo[2.2.2]octane-3,5'(4'H)-oxazole) 2.1 hydrochloride hydrate A solution of methyl (1,5-dimethyl-1H-indol-3-yl) imidate hydrochloride (0.37 g, 1.55 mmol) in methanol (30 ml) was added to a solution of 3-aminomethyl-3-hydroxy-1-azabicyclo[2.2.2]octane borane complex (0.29 g, 1.70 mmol) in methanol (15 ml). After heating at reflux for 24 hours, methanolic hydrogen chloride (30 ml) was added and the reaction mixture was heated under reflux for 3 hours. After evaporation the residue was dissolved in water and washed with dichloromethane. The aqueous phase was basified with ammonium hydroxide and extracted with dichloromethane (3×100 ml). The combined extracts were washed (H₂O), dried (MgSO₄) and solvents evaporated. The residue was dissolved in ethanol and treated with ethereal hydrogen chloride to give the title compound (0.35 g) m.p. 242°-3° C. Found: C, 56.47; H, 6.68; N, 10.35; Cl, 18.53; $C_{19}H_{23}N_3O$.2.1HCl.H₂O requires C, 56.49; H, 6.76; N, 10.40; Cl, 18.53%; δ$_H$ (360 MHz, D₂O) 2.02-2.32 (3H, m, 1 of CH₂ and CH₂), 2.44-2.58 (4H, m, CHH and CH₃), 2.72-2.78 (1H, m, CH), 3.42-3.52 (2H, m, CH₂), 3.56-3.74 (2H, m, CH₂), 3.87 (1H, d, J=15.1, CHHN), 3.94 (3H, s, NCH₃), 4.11 (1H, d, J=15.1, CHHN), 4.21 (1H, d, J=12, CHHN), 4.50 (1H, d, J=12, CHHN), 7.36 (1H, d, J=8.4, CH), 7.57 (1H, d, J=8.5, CH), 7.68 (1H, s, CH), 8.35 (1H, s, CH); m/z 309 M+.

EXAMPLE 29

[2'-(1,7-Dimethyl-1H-indol-3-yl)-]spiro(1-azabicyclo[2.2.2]octane-3,5'(4'H)-oxazole) 2.1 hydrochloride 1.5 hydrate (a) Methyl (1,7-dimethyl-1H-indol-3-yl) imidate hydrochloride Following the method of 28a 1,7-dimethyl-1H-indole-3-nitrile (0.75 g, 4.4 mmol) was reacted to give the title compound (0.76 g), m.p. 205°-7° C.; δ$_H$ (360 MHz, DMSO-d₆), 2.76 (3H, s, CH₃), 4.17 (3H, s, NCH₃), 4.27 (3H, s, OCH₃), 7.07 (1H, d, J=7.2, CH), 7.17 (1H, t, J=7.5, CH), 7.77 (1H, d, J=8.1, CH), 8.66 (1H, s, CH); m/z 202 M+.

(b) [2'(1,7-Dimethyl-1H-indol-3-yl)-]spiro(1-azabicyclo[2.2.2]octane-3,5'(4'H) oxazole 2.1) hydrochloride 1.5 hydrate Following the method of 28b methyl (1,7-dimethyl-1H-indole-3-yl) imidate hydrochloride (0.24 g, 1.0 mmol) and 3-aminomethyl-3-hydroxy-1-azabicyclo[2.2.2]octane borane complex (0.19 g, 1.1 mmol) were reacted to give the title compound (0.18 g), m.p. 204°–6° C. Found: C, 55.33; H, 6.81; N, 10.20; CL 17.88; $C_{19}H_{23}N_3O.2.1$ HCl.1.5H$_2$O requires C, 55.26; H, 6.86; N, 10.17; Cl, 18.03; $\delta_H$ (360 MHz, D$_2$O) 1.98–2.28 (3H, m, CHH and CH$_2$), 2.44–2.54 (1H, m, CHH), 2.66–2.72 (1H, m, CH), 2.78 (3H, s, CH$_3$), 3.38–3.46 (2H, m, CH$_2$N), 3.52–3.68 (2H, m, CH$_2$N), 3.81 (1H, d, J=15, CHHN), 4.06 (1H, d, J=15, CHHN), 4.15 (1H, d, J=12.4, CHHN), 4.18 (3H, s, NCH$_3$), 4.43 (1H, d, J=12.4, CHHN), 7.19 (1H, d, J=7.3, CH), 7.29 (1H, t, J=7.8, CH), 7.76 (1H, d, J=7.9, CH), 8.22 (1H, s, CH); m/z 309 (M+, free base).

EXAMPLE 30

[2'-(1-Methyl-1H-indol-3-yl)-]spiro(8-azabicyclo[3.2.1]octane-3,5'-(4'H)oxazole) dihydrochloride hydrate

[8-Benzyl-2'-(1-methyl-1H-indol-3-yl)-]spiro(8-azabicyclo[3.2.1]octane-3,5'-(4'H)oxazole) dihydrochloride dihydrate (0.095 g, 0.2 mmol) in methanol was shaken with 10% palladium on carbon under hydrogen at 45 psi for 6 hours. The catalyst was filtered and methanol evaporated. The residue was crystallised from methanol/ether to give the title compound (0.035 g) m.p. 196°–8° C.; $\delta_H$(360 MHz, D$_2$O), 2.16–2.30 (4H, m, two of CH$_2$), 2.60 (2H, d, J=12.5, CH$_2$), 2.68 (2H, dd, J=15.1, 3.3, CH$_2$), 3.95 (3H, s, NCH$_3$), 4.34–4.40 (4H, m, 2×CH and CH$_2$N), 7.44 (1H, dt, J=7.2, 1.1, CH), 7.49 (1H, dt, J=7.2, 1.3, CH), 7.66 (1H, dd, J=7.5, 1.4, CH), 7.98 (1H, dd, J=7.1, 1.5, CH), 8.26 (1H, s, CH); m/z 295 (M+, free base).

EXAMPLE 31

Tablet Preparation

Tablets containing 1.0, 2.0, 25.0, 26.0, 50.0 and 100.0 mg, respectively, of the following compounds are prepared as illustrated below:

[2'-(1-Methyl-1H-indol-3-yl)-]spiro(1-azabicyclo[2.2.2]octane-3,5'(4'H)-oxazole)

[8-Methyl-2'-(1-methyl-1H-indol-3-yl)-]spiro(8-azabicyclo[3.2.1]octane-3,5'(4'H)-oxazole)

[2'-(5-Fluoro-1-methyl-1H-indol-3-yl)-]spiro(1-azabicyclo[2.2.2]octane-3,5'(4'H)-oxazole)

[2'-(1H-Indol-3-yl)-]spiro(1-azabicyclo[2.2.2]octane-3,5'(4'H)-oxazole)

[2'-(1-Methyl-1H-indol-3-yl)-]spiro(1-azabicyclo[3.3.1]nonane-4,5'(4'H)-oxazole)

[2'-(1-Cyclopropylmethyl-1H-indol-3-yl)-]spiro(1-azabicyclo[2.2.2]octane-3,5'(4'H)oxazole)

[2'-(1-Methyl-1H-indol-3-yl)-]spiro(1-azabicyclo[2.2.1]heptane-3,5'(4'H)-oxazole)

| TABLE FOR DOSES CONTAINING FROM 1-25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100.0 mg of active ingredient per tablet.

What is claimed is:

1. A compound of formula I or a salt or prodrug thereof:

(I)

wherein the dotted line represents an optional chemical bond in one of the two possible positions;

A represents a group of formula II:

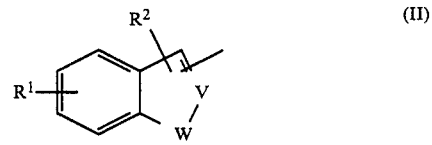

(II)

in which $R^1$ is selected from the group consisting of hydrogen, hydroxy, $C_{1-6}$ alkyl, $C_{2-6}$ alkenyl, $C_{2-6}$ alkynyl, $C_{1-6}$ alkoxy, benzyloxy, hydroxy($C_{1-6}$)alkyl, halogen, amino, cyano, nitro, —CONR$^6$R$^7$ and —SO$_2$NR$^6$R$^7$, in which R$^6$ and R$^7$ are independently selected from the group consisting of hydrogen, $C_{1-6}$ alkyl, $C_{2-6}$ alkenyl and $C_{2-6}$ alkynyl;

$R^2$ is selected from the group consisting of hydrogen, halogen, $C_{1-6}$ alkyl, $C_{1-6}$ alkoxy and $C_{1-6}$ alkylcarbonyl;

V represents nitrogen,

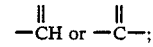

and

W represents oxygen, sulphur or

in which R$^8$ is selected from the group consisting of hydrogen, $C_{1-6}$ alkyl, $C_{2-6}$ alkenyl and $C_{2-6}$ alkynyl;

two of X, Y and Z are the same or different and each represents oxygen, sulphur or nitrogen; and the remaining group X, Y or Z is carbon, or Y is carbonyl (C=O); and Q is the residue of an azacyclic or azabicyclic ring system.

2. A compound according to claim 1 wherein A represents an indole of structure IIB:

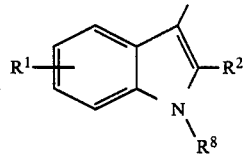

(IIB)

wherein $R^1$, $R^2$ and $R^8$ are as defined in claim 1.

3. A compound according to claim 1 wherein the azacyclic or azabicyclic ring system of which Q is the residue is selected from the group consisting of pyrrolidine, piperidine, tetrahydropyridine, azanorbornane, quinuclidine, isoquinuclidine, azabicyclo[3.2.1]octane and azabicyclo[3.3.1]nonane, any of which may be optionally substituted with methyl or hydroxy.

4. A compound according to claim 1 represented by formula III:

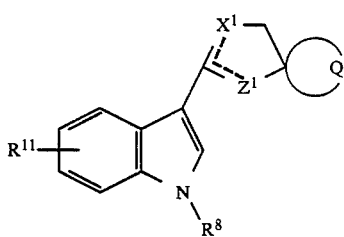

(III)

wherein $R^8$, Q and the dotted line are as defined in claim 1; $X^1$ and $Z^1$ independently represent oxygen, sulphur or nitrogen; and $R^{11}$ is selected from the group consisting of hydrogen, hydroxy, $C_{1-6}$ alkyl, $C_{1-6}$ alkoxy, halogen, amino and nitro.

5. A compound according to claim 4 wherein Q represents the residue of an optionally substituted ring system selected from the group consisting of piperidine, azanorbornane, quinuclidine, 8-azabicyclo[3.2.1]octane and 1-azabicyclo[3.3.1]nonane.

6. A compound according to claim 1 selected from:
[2'-(1-methyl-1H-indol-3-yl)]spiro(1-azabicyclo[2.2.2]octane-3,5'(4'H)-oxazole);
[8-methyl-2'-(1-methyl-1H-indol-3-yl)]spiro(8-azabicyclo[3.2.1]octane-3,5'(4'H)-oxazole);
[8-benzyl-2'-(1-methyl-1H-indol-3-yl)]spiro(8-azabicyclo[3.2.1]octane-3,5'(4'H)-oxazole);
[2'-(5-fluoro-1-methyl-1H-indol-3-yl)]spiro(1-azabicyclo[2.2.2]octane-3,5'(4'H)-oxazole);
[8-methyl-2'-(5-fluoro-1-methyl-1H-indol-3-yl)]spiro(8-azabicyclo[3.2.1]octane-3,5'(4'H)-oxazole);
[2'-(1H-indol-3-yl)]spiro(1-azabicyclo[2.2.2]octane-3,5'(4'H)-oxazole);
[2'-(1-methyl-1H-indol-3-yl)]spiro(1-azabicyclo[3.3.1]nonane-4,5'(4'H)-oxazole);
[2'-(1-cyclopropylmethyl-1H-indol-3-yl)]spiro(1-azabicyclo[2.2.2]octane-3,5'(4'H)-oxazole);
[2'-(1-ethyl-1H-indol-3-yl)]spiro(1-azabicyclo[2.2.2]octane-3,5'(4'H)-oxazole);
[2'-(5-nitro-1H-indol-3-yl)]spiro(1-azabicyclo[2.2.2]octane-3,5'(4'H)-oxazole);
[2'-(1-methyl-1H-indol-3-yl)]spiro(1-methylpiperidine-4,5'(4'H)-oxazole);
[2'-(1-methyl-1H-indol-3-yl)]spiro(1-azabicyclo[2.2.1]heptane-3,5'(4'H)-oxazole);
[2'-(1-methyl-1H-indol-3-yl)]spiro(1-methyl-1-azoniabicyclo[2.2.2]octane-3,5'(4'H)-oxazole) iodide;
[2'-(benzo(b)thiophen-3-yl)]spiro(1-azabicyclo[2.2.2]octane-3,5'(4'H)-oxazole);
[2'-(1-propyn-2-yl-1H-indol-3-yl)]spiro(1-azabicyclo[2.2.2]octane-3,5'(4'H)-oxazole);
[2'-(1-propen-2-yl-1H-indol-3-yl)]spiro(1-azabicyclo[2.2.2]octane-3,5'(4'H)-oxazole);
[2'-(5-amino-1-methyl-1H-indol-3-yl)]spiro(1-azabicyclo[2.2.2]octane-3,5'(4'H)-oxazole);
[2'-(2-iodo-1-methyl-1H-indol-3-yl)]spiro(1-azabicyclo[2.2.2]octane-3,5'(4'H)-oxazole);
[2'-(1H-indazol-3-yl)]spiro(1-azabicyclo[2.2.2]octane-3,5'(4'H)-oxazole);
[2'-(5-nitro-1-methyl-1H-indol-3-yl)]spiro(1-azabicyclo[2.2.2]octane-3,5'(4'H)-oxazole);
[2'-(5-methoxy-1-methyl-1H-indol-3-yl)]spiro(1-azabicyclo[2.2.2]octane-3,5'(4'H)-oxazole);
[2'-(5-hydroxy-1-methyl-1H-indol-3-yl)]spiro(1-azabicyclo[2.2.2]octane-3,5'(4'H)-oxazole);
[2'-(1,5-dimethyl-1H-indol-3-yl)]spiro(1-azabicyclo[2.2.2]octane-3,5'(4'H)-oxazole);
[2'-(1,7-dimethyl-1H-indol-3-yl)]spiro(1-azabicyclo[2.2.2]octane-3,5'(4'H)-oxazole);
[2'-(1-methyl-1H-indol-3-yl)]spiro(8-azabicyclo[3.2.1]octane-3,5'(4'H)-oxazole);
[2'-(1-methyl-1H-indol-3-yl)]spiro(1-azabicyclo[2.2.2]octane-3,4'(5'H)-oxazole);
and salts and prodrugs thereof.

7. A pharmaceutical composition for the treatment of psychotic disorders; anxiety; alcohol or drug withdrawal or dependence; pain; gastric stasis; gastric dysfunction; migraine; nausea and vomiting; movement disorders; or presenile and senile dementia; comprising an effective amount for the intended purpose of a compound according to claim 1 in association with a pharmaceutically acceptable carrier or excipient.

8. A method for the treatment of psychotic disorders; anxiety; alcohol or drug withdrawal or dependence; pain; gastric stasis; gastric dysfunction; migraine, nausea and vomiting; movement disorders; and presenile and senile dementia; which method comprises administering to a patient in need of such treatment an effective amount of a compound according to claim 1.

* * * * *